United States Patent
Lee et al.

(10) Patent No.: US 11,219,375 B2
(45) Date of Patent: Jan. 11, 2022

(54) METHOD AND DEVICE FOR DETECTING BLOOD PRESSURE CALIBRATION TIME POINT

(71) Applicant: SAMSUNG ELECTRONICS CO., LTD., Suwon-si (KR)

(72) Inventors: Donghyun Lee, Suwon-si (KR); Sunok Jung, Suwon-si (KR); Seunghwan Shin, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 115 days.

(21) Appl. No.: 16/663,422

(22) Filed: Oct. 25, 2019

(65) Prior Publication Data
US 2020/0146563 A1    May 14, 2020

(30) Foreign Application Priority Data
Nov. 12, 2018  (KR) .................. 10-2018-0138370

(51) Int. Cl.
*A61B 5/0205*   (2006.01)
*A61B 5/00*    (2006.01)
(Continued)

(52) U.S. Cl.
CPC ........ *A61B 5/02055* (2013.01); *A61B 5/0002* (2013.01); *A61B 5/01* (2013.01);
(Continued)

(58) Field of Classification Search
CPC ... A61B 5/02055; A61B 5/0002; A61B 5/681; A61B 5/02125; A61B 5/721;
(Continued)

(56) References Cited

U.S. PATENT DOCUMENTS

2010/0081941 A1*  4/2010  Naghavi ............... A61B 5/015
                                                       600/481
2015/0327786 A1   11/2015  Lading et al.
(Continued)

OTHER PUBLICATIONS

Cao, Hung et al. (2017). Cuff-Less and Continuous Blood Pressure Monitoring: A Methodological Review. Technologies. 5. 21. 10.3390/technologies5020021. (Year: 2017).*

*Primary Examiner* — Carl H Layno
*Assistant Examiner* — Aya Ziad Bakkar
(74) *Attorney, Agent, or Firm* — Nixon & Vanderhye P.C.

(57) ABSTRACT

An electronic device includes a processor and memory, wherein the memory stores instructions that, when executed by the processor, control the electronic device to: determine a pulse arrival time (PAT) value, a heart rate (HR) value, and a pulse transit time (PTT) value from the second data, calculate a first blood pressure value (BP1) and a second blood pressure value (BP2) by applying the determined values to pulse wave velocity (PWV) algorithms of Equations 1 and 2, wherein $BP1 \cong a_1 PAT + b_1 HR + c_1$ ... Equation 1, $BP2 \cong a_2 \ln(PTT) + b_2$ ... Equation 2 in Equations 1 and 2, $a_1, a_2, b_1, b_2$, and $c_1$ are constant values for matching blood pressure values measured during calibration with blood pressure values measured by a cuff hemodynamometer, determine a calibration time point based at least in part on a difference between the first blood pressure value and the second blood pressure value, and provide guide information related to the calibration time point through a user interface based at least in part on the determination.

16 Claims, 18 Drawing Sheets

(51) Int. Cl.
    *A61B 5/01*          (2006.01)
    *A61B 5/11*          (2006.01)
    *A61B 5/024*        (2006.01)
    *A61B 5/021*        (2006.01)
    *A61B 5/1171*       (2016.01)

(52) U.S. Cl.
    CPC ........... *A61B 5/1118* (2013.01); *A61B 5/1171* (2016.02); *A61B 5/4809* (2013.01); *A61B 5/681* (2013.01); *A61B 5/721* (2013.01); *A61B 5/7475* (2013.01); *A61B 5/02125* (2013.01); *A61B 5/02427* (2013.01); *A61B 2560/0238* (2013.01); *A61B 2562/0219* (2013.01)

(58) Field of Classification Search
    CPC .......... A61B 5/4809; A61B 2560/0238; A61B 2562/0219; A61B 5/7475
    See application file for complete search history.

(56) References Cited

U.S. PATENT DOCUMENTS

2016/0302677 A1\* 10/2016 He ..................... A61B 5/02125
2018/0085011 A1\*  3/2018 Ma ......................... G06F 21/31

\* cited by examiner

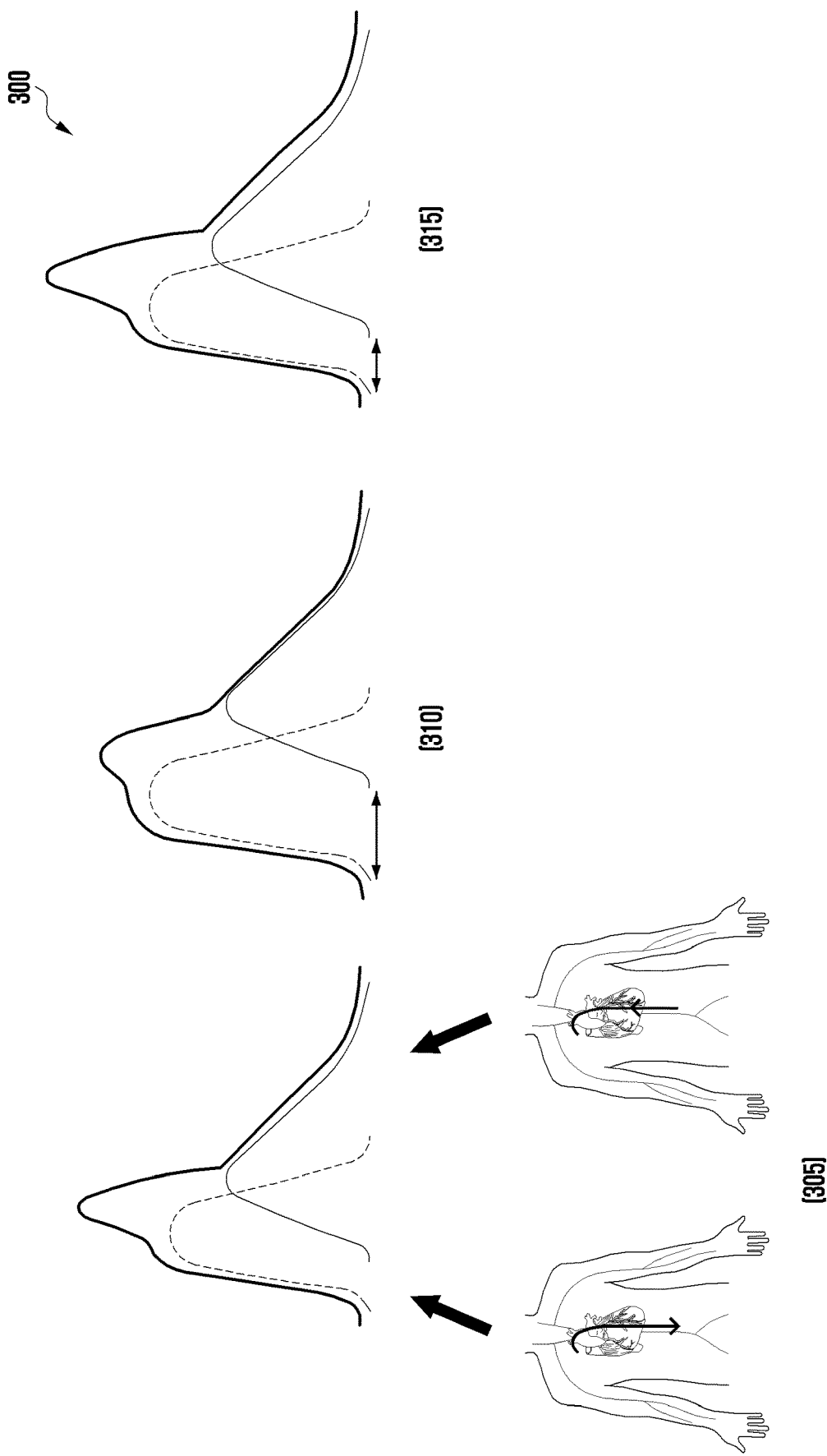

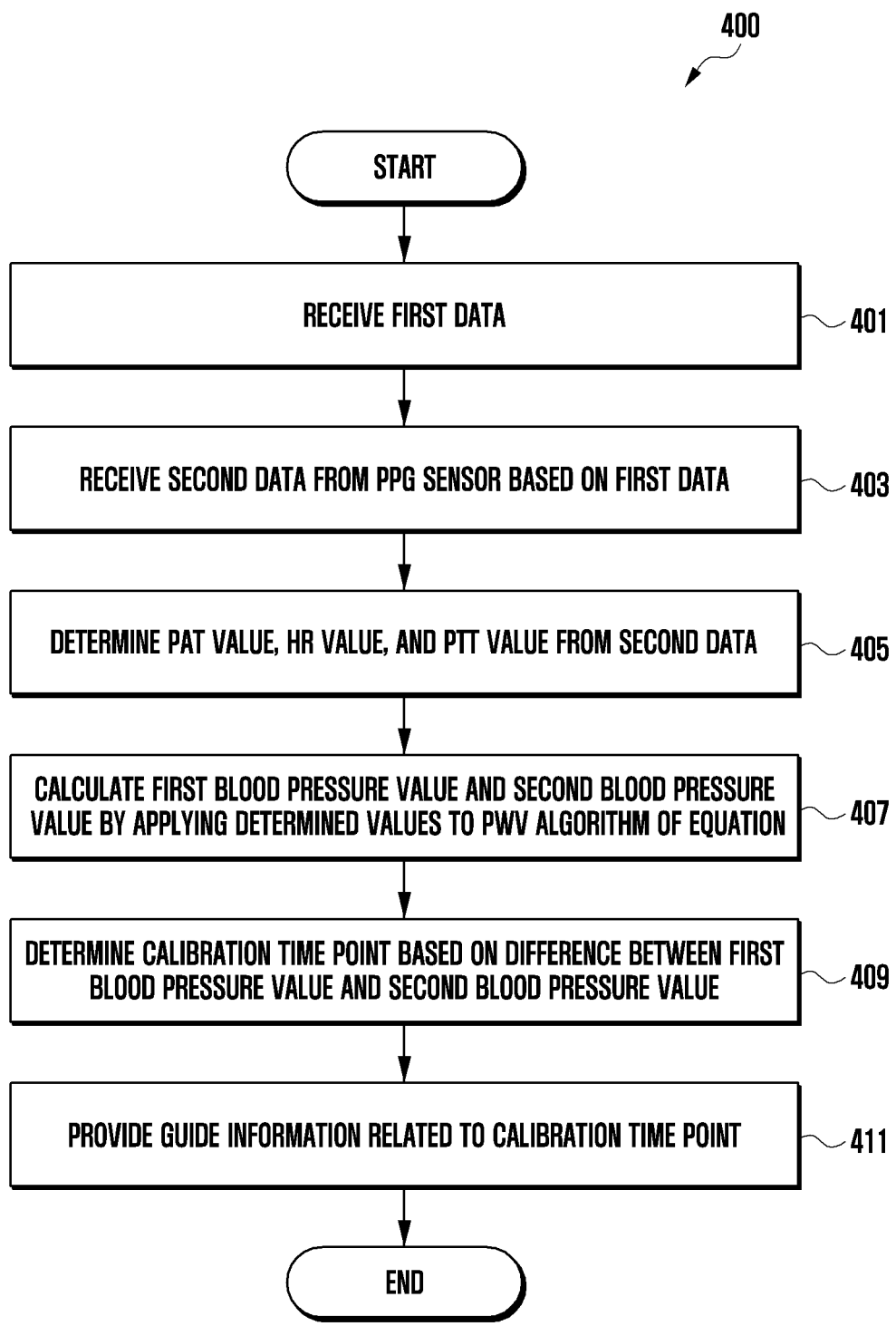

METHOD AND DEVICE FOR DETECTING BLOOD PRESSURE CALIBRATION TIME POINT

CROSS-REFERENCE TO RELATED APPLICATION

This application is based on and claims priority under 35 U.S.C. § 119 to Korean Patent Application No. 10-2018-0138370, filed on Nov. 12, 2018, in the Korean Intellectual Property Office, the disclosure of which is incorporated by reference herein in its entirety.

BACKGROUND

1) Field

The disclosure relates to a method and a device for detecting a blood pressure calibration time point.

2) Description of Related Art

As interests of the users in health have increased, various kinds of biometric information measuring devices have been developed. The methods for measuring biometric information may be largely classified into an invasive measurement method and a noninvasive measurement method. The noninvasive measurement methods, by which a pulse can be simply detected while pain is not caused to the user, have been widely used. For example, the noninvasive blood pressure measurement methods are methods for calculating a blood pressure without using a cuff, and may include pulse wave analysis (PWA), pulse wave velocity (PWV), and tonometry.

For example, the pulse wave analysis (PWA) is a method of estimating a blood pressure value based on the shapes of the waveforms measured in an optical scheme. The pulse waveform velocity (PWV) is a method of disposing sensors at different location of an artery and using a time interval between the pulses measured at two points. The tonometry is a method of disposing a pressure sensor on an artery at a base of a wrist, measuring the arterial pressure thereat, and estimating the blood pressure value of the coronary artery using the measured arterial pressure. Because all of the three listed methods are methods for indirectly estimating a blood pressure without directly actually measuring a blood pressure value of a coronary artery, a process of calibrating the results of the algorithms by a systolic blood pressure (SBP) and a diastolic blood pressure (DBP) which are actual blood pressure values is required.

Recently, with the development of digital technologies, various types of electronic devices have been widely utilized, such as, mobile communication terminals, personal digital assistants (PDA), electronic organizers, smart phones, tablet personal computers (PC), wearable devices, and the like. Further, the electronic device has continuously improved hardware parts and/or software parts thereof in order to support and increase functions. As an example, the electronic devices such as wearable devices are utilized as devices for measuring biometric information because they contact the human bodies of the users. The electronic devices calculate the blood pressure values of users and guide the measured blood pressure values to the users, and thus can allow the user to easily recognize to which degree the blood pressure of the user corresponds.

The blood pressure calibration may be a calibration which is performed on the result of the cuff-less hemodynamometer with a blood pressure measured by a cuff hemodynamometer after the blood pressure reference equipment (e.g. the cuff hemodynamometer) and the cuff-less hemodynamometer are operated simultaneously or sequentially. If the blood pressure calibration is not made, the user cannot obtain a precise blood pressure value in the cuff-less hemodynamometer, and thus may not detect a change of blood pressure, in particular, an abrupt increase of the blood pressure. The user has to input the blood pressure value measured by the cuff hemodynamometer when the blood pressure value is calculated first in the cuff-less hemodynamometer, and after then, the measurement of the blood pressure may be requested to be made again if the blood pressures measured by the cuff hemodynamometer and the cuff-less hemodynamometer are different by a preset value.

The proper time points of the blood pressure calibrations are different for different users, and may vary according to the body change degrees of the users. Accordingly, it may be difficult for the user to accurately recognize the blood pressure calibration time point of the user. This is because it may be necessary to calibrate the blood pressure at an interval of one month, one week, or one day according to the change of the body of the user, the mounting location of the wearable device, and a change in the mounting degree. Currently, in the cuff-less hemodynamometer, the calibration time point is informed of to all the users based on the experimental results of the manufacturer that manufactured the cuff-less hemodynamometer, and the user may fail to calibrate the blood pressure at a necessary time point or may have to further perform an unnecessary calibration operation.

Moreover, because the cuff-less hemodynamometer has to be used each time in order to recognize a more precise blood pressure calibration time point, it may be difficult to achieve the purpose of use of the cuff-less hemodynamometer. The user uses the cuff-less hemodynamometer to reduce disadvantages, such as inconveniences of the cuff hemodynamometer and inconveniences of movement of a device, and it may not be meaningful to use cuff-less hemodynamometer if the cuff hemodynamometer is frequently used to recognize a precise blood pressure correction time point.

The above information is presented as background information only to assist with an understanding of the disclosure. No determination has been made, and no assertion is made, as to whether any of the above might be applicable as prior art with regard to the disclosure.

SUMMARY

According to various embodiments, a method and a device for detecting and guiding a personalized blood pressure calibration time point by monitoring a difference between blood pressures measured by two different blood pressure measuring methods are disclosed.

In accordance with an example aspect of the disclosure, an electronic device includes housing, a user interface comprising interface circuitry disposed in a first part of the housing, a photoplethysmogram (PPG) sensor disposed to be exposed through a second part of the housing, the PPG sensor configured to calculate a blood pressure value while contacting a portion of a body of a user, at least one sensor, a wireless communication circuit disposed in the interior of the housing, a processor disposed in the interior of the housing, and operatively connected to the user interface, the PPG sensor, the at least one sensor, and the wireless communication circuit, and a memory operatively connected to the processor, wherein the memory stores instructions that, when executed by the processor, control the electronic device to: receive first data from the at least one sensor, receive second data from the PPG sensor based at least in part on the received first data, determine a pulse arrival time (PAT) value, a heart rate (HR) value, and a pulse transit time (PTT) value from the second data, calculate a first blood pressure value (BP1) and a second blood pressure value (BP2) by applying the determined values to pulse wave velocity (PWV) algorithms, wherein $BP1 \cong a_1 PAT + b_1 HR + c_1$, $BP2 \cong a_2 \ln(PTT) + b_2$, wherein, $a_1$, $a_2$, $b_1$, $b_2$, and $c_1$ are constant values for matching blood pressure values measured during calibration with blood pressure values measured by a cuff hemodynamometer, determine a calibration time point based at least in part on a difference between the first blood pressure value and the second blood pressure value, and provide guide information related to the calibration time point through the user interface based at least in part on the determination.

In accordance with another example aspect of the disclosure, an electronic device includes a housing, a user interface comprising interface circuitry disposed in a first part of the housing, a photoplethysmogram (PPG) sensor disposed to be exposed through a second part of the housing, the PPG sensor configured to calculate a blood pressure value while facing a portion of a body of a user, a wireless communication circuit disposed in the interior of the housing, a processor disposed in the interior of the housing and operatively connected to the user interface, the PPG sensor, and the wireless communication circuit, and a memory operatively connected to the processor, wherein the memory stores instructions that, when executed by the processor, control the electronic device to: receive data from the PPG sensor, determine a pulse arrival time (PAT) value, an heart rate (HR) value, and a pulse transit time (PTT) value from the data, calculate a first blood pressure value and a second blood pressure value by applying the determined values to a first pulse wave velocity (PWV) algorithm using the PAT value and the HR value and a second PWV algorithm using the PTT value, determine whether a calibration is necessary based at least in part on a difference between the first blood pressure value and the second blood pressure value, and provide information related to the calibration through the user interface based at least in part on the determination.

In accordance with another example aspect of the disclosure, an electronic device includes a housing, a user interface disposed in a first part of the housing, a photoplethysmogram (PPG) sensor disposed to be exposed through a second part of the housing, the PPG sensor configured to calculate a blood pressure value while contacting a portion of a body of a user, a wireless communication circuit disposed in the interior of the housing, a processor disposed in the interior of the housing, and operatively connected to the user interface, the PPG sensor, and the wireless communication circuit, and a memory operatively connected to the processor, wherein the memory stores instructions that, when executed by the processor, control the electronic device to: receive data from the PPG sensor, determine a pulse transit time (PTT) value, a cardiac output (CO) value, and a total peripheral resistance (TPR) value from the data, calculate a first blood pressure value and a second blood pressure by applying the determined values to a first pulse wave velocity (PWV) algorithm using the PTT value and a second pulse wave analysis (PWA) algorithm using the CO value and the TPR value, determine whether a calibration is necessary based at least in part on a difference between the first blood pressure value and the second blood pressure value, and provide information related to the calibration through the user interface based at least in part on the determination.

BRIEF DESCRIPTION OF THE DRAWINGS

The above and other aspects, features and advantages of certain embodiments of the present disclosure will be more apparent from the following detailed description, taken in conjunction with the accompanying drawings, in which:

FIG. 3A is a diagram illustrating an example of calculating a blood pressure value by analyzing a pulse waveform in an electronic device according to various embodiments;

FIG. 4 is a flowchart illustrating an example method of operating an electronic device according to various embodiments;

DETAILED DESCRIPTION

Figure 1:
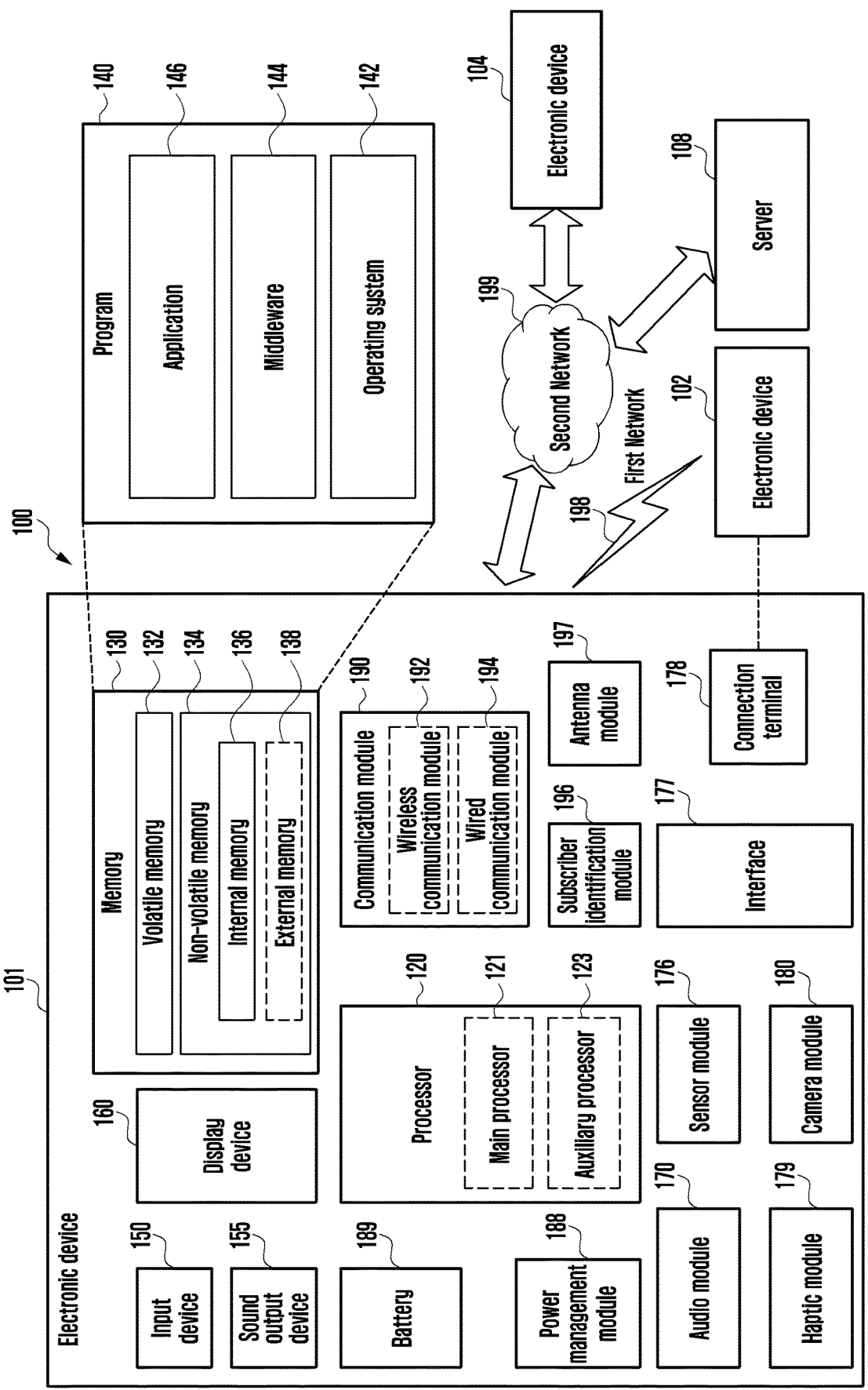
FIG. 1 is a block diagram illustrating an example electronic device in a network environment according to various embodiments.

The electronic device according to various embodiments may be one of various types of electronic devices. The electronic devices may include, for example, and without limitation, a portable communication device (e.g., a smart phone), a computer device, a portable multimedia device, a portable medical device, a camera, a wearable device, a home appliance, or the like. According to an embodiment of the disclosure, the electronic devices are not limited to those described above.

It should be appreciated that various embodiments of the present disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. It is to be understood that a singular form of a noun corresponding to an item may include one or more of the things, unless the relevant context clearly indicates otherwise. As used herein, each of such phrases as "A or B," "at least one of A and B," "at least one of A or B," "A, B, or C," "at least one of A, B, and C," and "at least one of A, B, or C," may include all possible combinations of the items enumerated together in a corresponding one of the phrases. As used herein, such terms as "1st" and "2nd," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with," "coupled to," "connected with," or "connected to" another element (e.g., a second element), the element may be coupled with the other element directly (e.g., wiredly), wirelessly, or via a third element.

As used herein, the term "module" may include a unit implemented in hardware, software, or firmware, or any combination thereof, and may interchangeably be used with other terms, for example, "logic," "logic block," "part," or "circuitry". A module may be a single integral component, or a minimum unit or part thereof, adapted to perform one or more functions. For example, according to an embodiment, the module may be implemented in a form of an application-specific integrated circuit (ASIC).

FIG. 1 is a block diagram illustrating an electronic device 101 in a network environment 100 according to various embodiments.

Referring to FIG. 1, the electronic device 101 in the network environment 100 may communicate with an electronic device 102 via a first network 198 (e.g., a short-range wireless communication network), or an electronic device 104 or a server 108 via a second network 199 (e.g., a long-range wireless communication network). According to an embodiment, the electronic device 101 may communicate with the electronic device 104 via the server 108. According to an embodiment, the electronic device 101 may include a processor 120, memory 130, an input device 150, a sound output device 155, a display device 160, an audio module 170, a sensor module 176, an interface 177, a haptic module 179, a camera module 180, a power management module 188, a battery 189, a communication module 190, a subscriber identification module (SIM) 196, or an antenna module 197. In some embodiments, at least one (e.g., the display device 160 or the camera module 180) of the components may be omitted from the electronic device 101, or one or more other components may be added in the electronic device 101. In some embodiments, some of the components may be implemented as single integrated circuitry. For example, the sensor module 176 (e.g., a fingerprint sensor, an iris sensor, or an illuminance sensor) may be implemented as embedded in the display device 160 (e.g., a display).

The processor 120 may execute, for example, software (e.g., a program 140) to control at least one other component (e.g., a hardware or software component) of the electronic device 101 coupled with the processor 120, and may perform various data processing or computation. According to an example embodiment, as at least part of the data processing or computation, the processor 120 may load a command or data received from another component (e.g., the sensor module 176 or the communication module 190) in volatile memory 132, process the command or the data stored in the volatile memory 132, and store resulting data in non-volatile memory 134. According to an embodiment, the processor 120 may include a main processor 121 (e.g., a central processing unit (CPU) or an application processor (AP)), and an auxiliary processor 123 (e.g., a graphics processing unit (GPU), an image signal processor (ISP), a sensor hub processor, or a communication processor (CP)) that is operable independently from, or in conjunction with, the main processor 121. Additionally or alternatively, the auxiliary processor 123 may be adapted to consume less power than the main processor 121, or to be specific to a specified function. The auxiliary processor 123 may be implemented as separate from, or as part of the main processor 121.

The auxiliary processor 123 may control at least some of functions or states related to at least one component (e.g., the display device 160, the sensor module 176, or the communication module 190) among the components of the electronic device 101, instead of the main processor 121 while the main processor 121 is in an inactive (e.g., sleep) state, or together with the main processor 121 while the main processor 121 is in an active state (e.g., executing an application). According to an embodiment, the auxiliary processor 123 (e.g., an image signal processor or a communication processor) may be implemented as part of another component (e.g., the camera module 180 or the communication module 190) functionally related to the auxiliary processor 123.

The memory 130 may store various data used by at least one component (e.g., the processor 120 or the sensor module 176) of the electronic device 101. The various data may include, for example, software (e.g., the program 140) and input data or output data for a command related thereto. The memory 130 may include the volatile memory 132 or the non-volatile memory 134.

The program 140 may be stored in the memory 130 as software, and may include, for example, an operating system (OS) 142, middleware 144, or an application 146.

The input device 150 may receive a command or data to be used by other component (e.g., the processor 120) of the electronic device 101, from the outside (e.g., a user) of the electronic device 101. The input device 150 may include, for example, a microphone, a mouse, or a keyboard.

The sound output device 155 may output sound signals to the outside of the electronic device 101. The sound output device 155 may include, for example, a speaker or a receiver. The speaker may be used for general purposes, such as playing multimedia or playing record, and the receiver may be used for an incoming calls. According to an embodiment, the receiver may be implemented as separate from, or as part of the speaker.

The display device 160 may visually provide information to the outside (e.g., a user) of the electronic device 101. The display device 160 may include, for example, a display, a hologram device, or a projector and control circuitry to control a corresponding one of the display, hologram device, and projector. According to an embodiment, the display device 160 may include touch circuitry adapted to detect a touch, or sensor circuitry (e.g., a pressure sensor) adapted to measure the intensity of force incurred by the touch.

The audio module 170 may convert a sound into an electrical signal and vice versa. According to an embodiment, the audio module 170 may obtain the sound via the input device 150, or output the sound via the sound output device 155 or a headphone of an external electronic device (e.g., an electronic device 102) directly (e.g., wiredly) or wirelessly coupled with the electronic device 101.

The sensor module 176 may detect an operational state (e.g., power or temperature) of the electronic device 101 or an environmental state (e.g., a state of a user) external to the electronic device 101, and then generate an electrical signal or data value corresponding to the detected state. According to an embodiment, the sensor module 176 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 177 may support one or more specified protocols to be used for the electronic device 101 to be coupled with the external electronic device (e.g., the electronic device 102) directly (e.g., wiredly) or wirelessly. According to an embodiment, the interface 177 may include, for example, a high definition multimedia interface (HDMI), a universal serial bus (USB) interface, a secure digital (SD) card interface, or an audio interface.

A connecting terminal 178 may include a connector via which the electronic device 101 may be physically connected with the external electronic device (e.g., the electronic device 102). According to an embodiment, the connecting terminal 178 may include, for example, a HDMI connector, a USB connector, a SD card connector, or an audio connector (e.g., a headphone connector).

The haptic module 179 may convert an electrical signal into a mechanical stimulus (e.g., a vibration or a movement) or electrical stimulus which may be recognized by a user via his tactile sensation or kinesthetic sensation. According to an embodiment, the haptic module 179 may include, for example, a motor, a piezoelectric element, or an electric stimulator.

The camera module 180 may capture a still image or moving images. According to an embodiment, the camera module 180 may include one or more lenses, image sensors, image signal processors, or flashes.

The power management module 188 may manage power supplied to the electronic device 101. According to an example embodiment, the power management module 188 may be implemented as at least part of, for example, a power management integrated circuit (PMIC).

The battery 189 may supply power to at least one component of the electronic device 101. According to an embodiment, the battery 189 may include, for example, a primary cell which is not rechargeable, a secondary cell which is rechargeable, or a fuel cell.

The communication module 190 may support establishing a direct (e.g., wired) communication channel or a wireless communication channel between the electronic device 101 and the external electronic device (e.g., the electronic device 102, the electronic device 104, or the server 108) and performing communication via the established communication channel. The communication module 190 may include one or more communication processors that are operable independently from the processor 120 (e.g., the application processor (AP)) and supports a direct (e.g., wired) communication or a wireless communication. According to an embodiment, the communication module 190 may include a wireless communication module 192 (e.g., a cellular communication module, a short-range wireless communication module, or a global navigation satellite system (GNSS) communication module) or a wired communication module 194 (e.g., a local area network (LAN) communication module or a power line communication (PLC) module). A corresponding one of these communication modules may communicate with the external electronic device via the first network 198 (e.g., a short-range communication network, such as Bluetooth™, wireless-fidelity (Wi-Fi) direct, or infrared data association (IrDA)) or the second network 199 (e.g., a long-range communication network, such as a cellular network, the Internet, or a computer network (e.g., LAN or wide area network (WAN)). These various types of communication modules may be implemented as a single component (e.g., a single chip), or may be implemented as multi components (e.g., multi chips) separate from each other. The wireless communication module 192 may identify and authenticate the electronic device 101 in a communication network, such as the first network 198 or the second network 199, using subscriber information (e.g., international mobile subscriber identity (IMSI)) stored in the subscriber identification module 196.

The antenna module 197 may transmit or receive a signal or power to or from the outside (e.g., the external electronic device) of the electronic device 101. According to an embodiment, the antenna module 197 may include one or more antennas, and, therefrom, at least one antenna appropriate for a communication scheme used in the communication network, such as the first network 198 or the second network 199, may be selected, for example, by the communication module 190 (e.g., the wireless communication module 192). The signal or the power may then be transmitted or received between the communication module 190 and the external electronic device via the selected at least one antenna.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment, commands or data may be transmitted or received between the electronic device 101 and the external electronic device 104 via the server 108 coupled with the second network 199. Each of the electronic devices 102 and 104 may be a device of a same type as, or a different type, from the electronic device 101. According to an embodiment, all or some of operations to be executed at the electronic device 101 may be executed at one or more of the external electronic devices 102, 104, or 108. For example, if the electronic device 101 should perform a function or a service automatically, or in response to a request from a user or another device, the electronic device 101, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 101. The electronic device 101 may provide the outcome, with or without further processing of the outcome, as at least part of a reply to the request. To that end, a cloud computing, distributed computing, or client-server computing technology may be used, for example.

Various embodiments as set forth herein may be implemented as software (e.g., the program 140) including one or more instructions that are stored in a storage medium (e.g., internal memory 136 or external memory 138) that is readable by a machine (e.g., the electronic device 101). For example, a processor (e.g., the processor 120) of the machine (e.g., the electronic device 101) may invoke at least one of the one or more instructions stored in the storage medium, and execute it, with or without using one or more other components under the control of the processor. This allows the machine to be operated to perform at least one function according to the at least one instruction invoked. The one or more instructions may include a code generated by a complier or a code executable by an interpreter. The machine-readable storage medium may be provided in the form of a non-transitory storage medium. Wherein, the "non-transitory" storage medium is a tangible device, and may not include a signal (e.g., an electromagnetic wave), but this term does not differentiate between where data is semi-permanently stored in the storage medium and where the data is temporarily stored in the storage medium.

According to an embodiment, a method according to various embodiments of the disclosure may be included and provided in a computer program product. The computer program product may be traded as a product between a seller and a buyer. The computer program product may be distributed in the form of a machine-readable storage medium (e.g., compact disc read only memory (CD-ROM)), or be distributed (e.g., downloaded or uploaded) online via an application store (e.g., Play Store™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to various embodiments, each component (e.g., a module or a program) of the above-described components may include a single entity or multiple entities. According to various embodiments, one or more of the above-described components may be omitted, or one or more other components may be added. Alternatively or additionally, a plurality of components (e.g., modules or programs) may be integrated into a single component. In such a case, according to various embodiments, the integrated component may still perform one or more functions of each of the plurality of components in the same or similar manner as they are performed by a corresponding one of the plurality of components before the integration. According to various embodiments, operations performed by the module, the program, or another component may be carried out sequentially, in parallel, repeatedly, or heuristically, or one or more of the operations may be executed in a different order or omitted, or one or more other operations may be added.

Figure 2A:
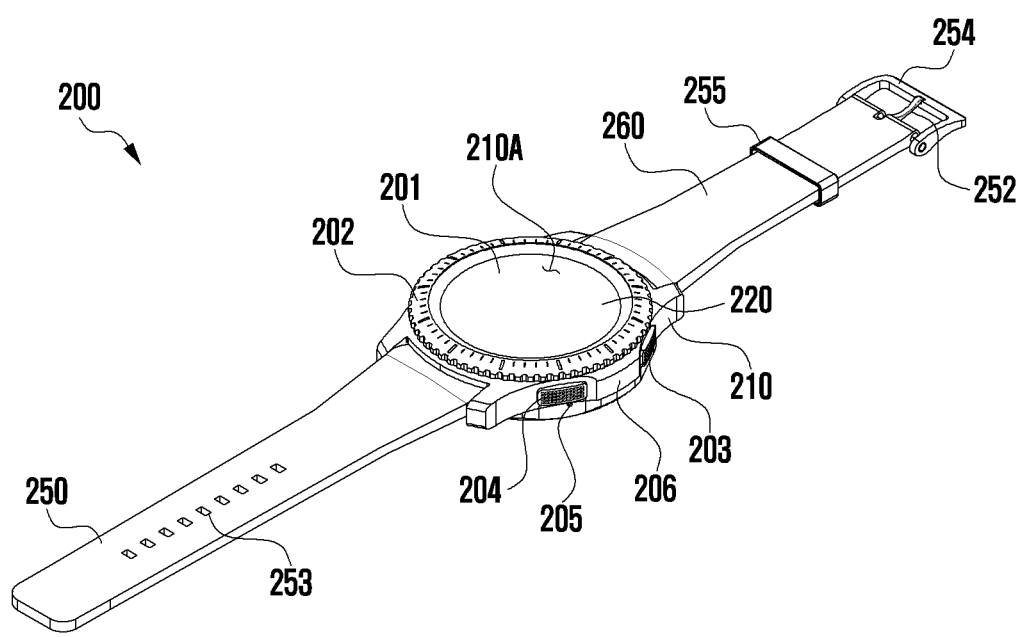
FIG. 2A is a front perspective view illustrating an example electronic device according to various embodiments.
Figure 2B:
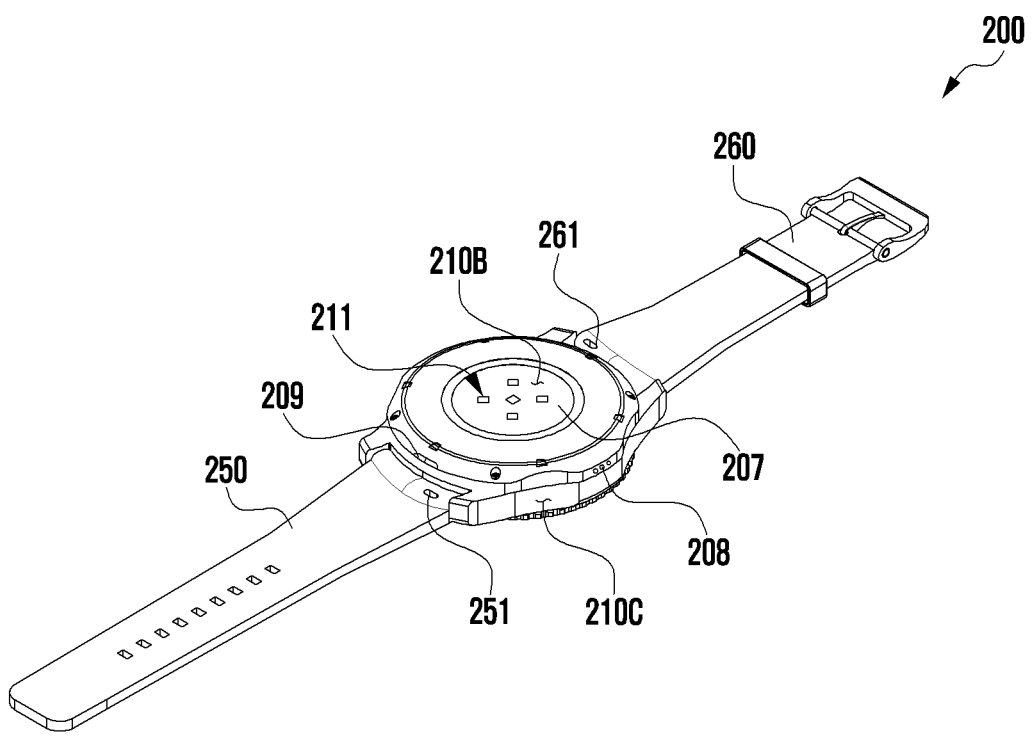
FIG. 2B is a rear perspective view illustrating an example electronic device according to various embodiments.

FIG. 2A is a front perspective view illustrating an example electronic device 200 according to various embodiments, and FIG. 2B is a rear perspective view illustrating the example electronic device 200 according to various embodiments.

Referring to FIGS. 2A and 2B, an electronic device 200 according to an embodiment (e.g., an electronic device 101 of FIG. 1) may include a housing 210 including a first surface (or a front surface) 210A, a second surface (or a rear surface) 210B, and a side surface 210C that surrounds a space between the first surface 210A and the second surface 210B, and fastening members 250 and 260 (e.g., straps) connected to at least portions of the housing 210 and configured to detachably fasten the electronic device 200 to a portion (e.g., a wrist, or an ankle) of the body of a user. In another embodiment (not illustrated), the housing may refer to a structure that defines some of the first surface 210A, the second surface 210B, and the side surface 210C of FIG. 2A. According to an embodiment, the first surface 210A may be defined by a front plate 201 (e.g., a glass plate or a polymer plate including various coating layers), at least a portion of which is substantially transparent. The second surface 210B may be defined by a rear plate 207 that is substantially opaque. The rear plate 207, for example, may be formed of coated or colored glass, ceramics, a polymer, a metal (e.g., aluminum, stainless steel (STS), or magnesium), or a combination of at least two thereof. The side surface 210C may be coupled to the front plate 201 and the rear plate 207, and may be defined by a side bezel structure (or 'a side member') 206 including a metal and/or a polymer. In some embodiments, the rear plate 207 and the side bezel structure 206 may be integrally formed and may include the same material (e.g., a metallic material such as aluminum). The fastening members 250 and 260 may be formed of various materials and may have various shapes. A single body or a plurality of unit links that may move with respect to each other may be formed of woven fabric, leather, rubber, urethane, a metal, ceramics, or a combination of at least two thereof.

According to an embodiment, the electronic device 200 may include at least one of a display 220 (e.g., a display device 160 of FIG. 1), audio modules 205 and 208, a sensor module 211, key input devices 202, 203, and 204, and a connector hole 209. In some embodiments, at least one (e.g., the key input devices 202, 203, and 204, the connector hole 209, or the sensor module 211) of the elements may be omitted from the electronic device 200 or another component may be additionally included in the electronic device 200.

The display 220 (e.g., the display device 160 of FIG. 1, or a user interface), for example, may be exposed through a first part (e.g., a corresponding part of the front plate 201). The shape of the display 220 may correspond to the shape of the front plate 201, and may include various shapes, such as a circular shape, an elliptical shape, or a polygonal shape. The display 220 may be coupled to or be disposed to be adjacent to a touch detection circuit, a pressure sensor that may measure the strength (the pressure) of a touch, and/or a fingerprint sensor.

The audio modules 205 and 208 may include a microphone hole 205 and a speaker hole 208. A microphone for acquiring external sounds may be disposed in the microphone hole 205, and in some embodiments, a plurality of microphones may be disposed to detect the direction of a sound. The speaker hole 208 may be used for an external speaker and a communication receiver. In some embodiments, the speaker holes 207 and the microphone hole 203 may be realized by one hole or a speaker may be included while the speaker holes 207 are not employed (e.g., a piezoelectric speaker).

The sensor module 211 may generate an electrical signal or a data value corresponding to an operation state of the interior of the electronic device 200 or an environmental state of the outside. The sensor module 211, for example, may include a biometric sensor module (e.g., an HRM sensor) exposed through the second surface 210B of the housing 210. The biometric sensor module may include a photoplethysmogram (PPG) configured to calculate a blood pressure value while contacting a portion of the body of the user. The sensor module 211 may include an electrode that may measure at least one of an electrocardiogram (ECG), a galvanic skin response (GSR), an electroencephalogram (EEG), a bioimpedence assessment (BIA), or a ballistocardiogram (BCG). The sensor module 211 may further include at least one sensor. The electronic device 200 may further include a sensor module (not illustrated), for example, at least one of a gesture sensor, a gyro sensor, an atmospheric pressure sensor, a magnetic sensor, an acceleration sensor, a grip sensor, a color sensor, an infrared (IR) sensor, a biometric sensor, a temperature sensor, a humidity sensor, or an illumination sensor.

According to various embodiments, when the sensor module 211 may include a biometric optical sensor, an LED having various N wavelengths may be provided as a light source. When a green wavelength is used for the light source, the green wavelength may be a wavelength band that is most widely used to measure a heart rate, and the green wavelength may penetrate into skin thin and have robust characteristics to noise in the sensor module 211. When a red wavelength is used for the light source, the red wavelength may penetrate relatively deep skin and the sensor module 211 may measure a heart rate more precisely. When an infrared (IR) wavelength is used for the light source, the sensor module 211 may acquire biometric information such as a heart rate and a saturation of percutaneous oxygen (SPO2), together with the red wavelength. When the red, green, and ultraviolet wavelengths are used for the light source, the sensor module 211 may measure a skin tone. When the blue wavelength is used for the light source, the sensor module 211 may measure the tendency of blood glucose. As more various LED wavelengths are added, much more biometric information may be acquired.

According to various embodiments, the sensor module 211 may variously include one or more wavelengths. The sensor module 211 may include one or more emitters and detectors for the wavelengths. For example, the detectors may include one or more photodiodes, may be spaced apart from the light source by the same interval, and one or more detectors may be configured to have different spacing distances. A sensor IC (not illustrated) may include a sensor driving controller that directly controls a sensor, and an analog-to-digital (A/D) converter. The sensor driving controller may include an emitter controller and a detector controller. The sensor driving controller may function to directly drive the emitter and the detector. The sensor driving controller may function as an analog front end (AFE). The analog front end may include LED drivers, an amplifier that amplifies detector values, an analog-to-digital converter that converts an analog value output from the detector to a digital value, and a controller that controls the LED drivers and the analog-to-digital converter. The sensor data input through the detector may be processed as biometric information and may be provided to the user. The biometric information may be stored in an application that provides biometric information, or may be provided in a third application.

The key input devices 202, 203, and 204 may include a wheel key 202 disposed on the first surface 210A of the housing 210 and being rotatable in at least one direction, and/or side key buttons 202 and 203 disposed on the side surface 210C of the housing 210. The wheel key may have a shape corresponding to the shape of the front plate 210. In another embodiment, the electronic device 200 may not include some or all of the above-mentioned key input devices 202, 203, and 204, and the key input devices 202, 203, and 204 which are not included, may be realized in different forms, such as a soft key, on the display 220. The connector hole 209 may accommodate a connector (e.g., a USB connector) for transmitting and receiving power and/or data to and from an external electronic device, and may include another connector hole (not illustrated) that may accommodate a connector for transmitting and receiving an audio signal to and from an external electronic device. The electronic device 200, for example, may further include a connector cover (not illustrated) configured to cover at least a portion of the connector hole 209 to prevent introduction of external foreign substances through the connector hole 109.

The fastening members 250 and 260 may be detachably fastened to at least a partial area of the housing 210 using locking members 251 and 261. The fastening members 250 and 260 may include one or more of a fixing member 252, a fixing member coupling hole 253, a band guide member 254, and a band fixing ring 255.

The fixing member 252 may be configured to fix the housing 210 and the fastening members 250 and 260 to a portion (e.g., a wrist or a wrinkle) of the body of the user. The fixing member coupling hole 253 may fix the housing 210 and the fastening members 250 and 260 to a portion of the body of the user in correspondence to the fixing member 252. The band guide member 254 may be configured to restrict a motion range of the fixing member 252 when the fixing member 252 is coupled to the fixing member coupling hole 253 so that the fastening members 250 and 260 are fastened to be attached to a portion of the body of the user. The band fixing ring 255 may restrict motion ranges of the fastening members 250 and 260 in a state in which the fixing member 252 and the fixing member coupling hole 253 are coupled to each other.

According to various embodiments, the electronic device 200 may further include a wireless communication circuit (e.g., the communication module 190 of FIG. 1) located in the interior of the housing 210, a processor (e.g., the processor 120 of FIG. 1) located in the interior of the housing 210 and operatively connected to the user interface (e.g., the display 200), the PPG sensor, the at least one sensor, and the wireless communication circuit, and a memory (e.g., the memory 130 of FIG. 1) operatively connected to the processor. The memory 130 may store instructions that, when executed, cause the processor 120 to receive first data from the at least one sensor, receive second data from the PPG sensor at least partially based on the received first data, determine a pulse arrival time (PAT) value, a heart rate (HR) value, and a pulse transit time (PTT) value from the second data, calculate a first blood pressure value (BP1) and a second blood pressure value (BP2) by applying the determined values to a pulse wave velocity (PWV) algorithm, determine a calibration time point at least partially based on a difference between the first blood pressure value and the second blood pressure value, and provide guide information related to the calibration time point through the user interface, at least partially based on the determination. It will be understood that the descriptions herein referring to the processor being configured to perform various functions is not limited to the processor itself performing the various functions, but includes, without limitation, the electronic device performing the various functions under, for example, control of the processor, including the processor performing the various functions.

According to various embodiments, the processor 120 may recognize (or detect) a user state. The user state may be classified into a state having a motion and a state without a motion. The user state also may be classified into a static state, a dynamic state, or a sleep state. The user state also may include at least one of a static state, a dynamic state, a sleep state, or an exercise state. The user state is exemplary, and is not limited to the four states. The static state may refer, for example, to a state (e.g., a sedentary state) in which the user is seated. The dynamic state may refer, for example, to a state in which the user moves, and may refer, for example, to an active state in which it is difficult to measure a blood pressure. The sleep state may refer, for example, to a state in which there are few motions and a low blood pressure is maintained. The exercise state may refer, for example, to a state in which the heart rate increases abruptly, that is, a state in which there are motions that are larger than those of the dynamic state.

According to various embodiments, the processor 120 may recognize the user state using sensor data acquired by the sensor module 211. For example, when a difference between the acceleration data measured using the acceleration sensor and the previous acceleration data is small (e.g., when the difference is less than a first threshold), the processor 120 may determine the user state as a static state. When the difference between the acceleration data and the previous acceleration data is the first threshold or more and less than a second threshold, the processor 120 may determine the user state as a dynamic state. When the difference between the acceleration data and the previous acceleration data is not less than the second threshold that is larger than the first threshold, the processor 120 may determine the user state as an exercise state. When the sensor data (e.g., the acceleration data or gyro data) measured using the acceleration sensor or the gyro sensor satisfies a preset condition, the processor 120 may determine the user state as a static state. The preset condition may include a case in which the gyro data corresponds to a horizontal state or the acceleration data is not detected (or a case in which a difference between the acceleration data is small).

According to various embodiments, the state of the user may be recognized (or determined) to determine whether measurements of blood pressure according to the algorithms are possible in the current user state. For example, a possibility in which the blood pressure measured in a state (e.g., a dynamic state or an exercise state) with a motion is different from the actual blood pressure may be high. The blood pressure measured not by a cuff hemodynamometer but by the electronic device 101 in a state with a motion may not be trustworthy. The processor 120 may determine the degree of precision of the blood pressure measured through a pulse wave velocity (PWV) method or a pulse wave analysis (PWA) method based on the user state.

The processor 120 may calculate a blood pressure (or a blood pressure value). For example, the processor 120 may calculate a blood pressure value with a PWA or a PWV. Although it will be described below that a blood pressure value is calculated in two methods, the method of calculating a blood pressure value is not limited to the two methods. The PWA is a scheme of analyzing the waveform of a pulse with the sensor data acquired by the sensor module 211, extracting a feature point having a high correlation with the blood pressure, and calculating (or measuring) a blood pressure value using the feature point. For example, when the sensor module 211 includes a photoplethysmography module, a photoplethysmogram measured by the photoplethysmography module may include a feature point, such as an augmentation index (AI), an augmentation point (AP), a dicrotic notch, or an area. The processor 120 may acquire a cardiac output (CO) value, a total peripheral resistance (TPR) value, and the stiffness of a blood vessel, which are related to the feature point.

According to various embodiments, the PWV is a scheme of calculating a blood pressure value through measurement of the velocity of a blood flow. The PWV may be classified by a pulse arrival time (PAT) value and a pulse transit time (PTT) value. Both the PAT and PTT may measure a blood flow time using a time point at which blood starts and a time point at which the blood arrives, and may calculate the velocity of the blood flow. The processor 120 may estimate a blood pressure value using a proportional relationship between the calculated blood flow speed and the blood pressure.

According to various embodiments, the electronic device 200 may have difficulty in measuring a blood pressure precisely because the blood pressure value is not measured while a device (e.g., a cuff) for measuring a blood pressure is not attached to the user. The processor 120 may estimate (or calculate) a blood pressure value using the sensor data measured by the sensor module 211. The measured sensor data (e.g., a measurement parameter) may vary according to the type of the sensor included in the sensor module 211. The processor 120 may calculate a blood pressure value with, among various algorithms, at least two algorithms using the sensor data measured by the sensor module 211. For example, the processor 120 may receive first data from the at least one sensor, may receive second data from the PPG sensor at least partially based on the received first data, and may determine a pulse arrival time (PAT) value, a heart rate (HR) value, and a pulse transit time (PTT) value from the second data. The processor 120 may calculate blood pressure values of at least two times by changing the blood pressure calculating method (e.g., a PWA or a PWV) or changing a parameter or an equation used for calculating a blood pressure.

According to various embodiments, the processor 120 may calculate a first blood pressure value BP1 and a second blood pressure value BP2 by applying the determined values to the pulse wave velocity (PWV) algorithms of Equation 1 (or Formula 1) and Equation 2 (or Formula 2). Equations 1 and 2 may be as follows.

$$BP_1 \cong a_1 PAT + b_1 HR + c_1 \quad \text{[Equation 1]}$$

$$BP_2 \cong a_2 \ln(PTT) + b_2 \quad \text{[Equation 2]}$$

In Equations 1 and 2, $a_1$, $a_2$, $b_1$, $b_2$, and $c_1$ may be constant values for matching blood pressure values calculated during calibration with blood pressure values calculated by a cuff hemodynamometer.

The processor 120 may determine a calibration time point at least partially based on a difference between the first blood pressure value and the second blood pressure value, and may provide guide information related to the calibration time point through the user interface (e.g., the display 220), at least partially based on the determination.

According to various embodiments, the processor 120 may receive second data from the PPG sensor when the first data is a selected threshold value or less. The processor 120 may store the calculated blood pressure value in the memory 130 at least partially based on the difference between the first blood pressure value and the second blood pressure value. The processor 120 may receive a new pressure value from the user according to the guide information, and may store the new blood pressure value in the memory 130. The processor 120 may guide a precision for blood pressure until the new blood pressure value is input. The processor 120 may determine the constant values based on the new blood pressure, and may calculate the first blood pressure value and the second blood pressure value based on the determined constant values. For example, the processor 120 may determine the constant values of $a_1$, $a_2$, $b_1$, $b_2$, and $c_1$ as calibration factors in Equations 1 and 2.

According to various embodiments, the PWA or the PWV may include various equations for calculating a blood pressure. Although the conventional electronic device calculates a blood pressure value in a preset equation, the disclosure may calculate a blood pressure value using, among a plurality of equations, two or more different equations. According to various embodiments, the processor 120 may determine a blood pressure calculating method or equation based on the user state, and may calculate a blood pressure value based on the determined blood pressure calculating method or equation.

According to various embodiments, the processor 120 may determine whether it is possible to calculate a blood pressure with the algorithms, based on the user state. The PWA may achieve a calculation only when there is no motion because a clear waveform is necessary, and the PWV may achieve a calculation even in a state in which there is a degree of motion if a cardiogram or a pulse (or a heart rate) is used. In a state in which there is a motion, the calculated blood pressure of the PWA may be different from the actual blood pressure with a high possibility. In a state with a motion, the blood pressure calculated by the PWA and the blood pressure calculated by the PWV may be different. The processor 120 may determine whether the blood pressure will be calculated by the PWA or the blood pressure will be calculated by the PWV, based on the user state.

The processor 120 may calibrate the calculated blood pressure (or blood pressure value) with the actual blood pressure. Because both of the PWV and the PWA are not a method of measuring the actual pressure of a brachial artery even though they are a scheme of estimating a blood pressure value using indexes (a CO, a TPR, and the speed of a blood flow) related to a blood pressure, it may be necessary to calibrate the estimated blood pressure with the actual blood pressure. The processor 120 may calibrate a blood pressure value using Equation 3 in the PWV.

$$BP_{PWV} = -\frac{2}{\alpha}\ln(PTT) + \frac{1}{\alpha}\ln\left(\frac{2r\rho\Delta X^2}{Eh}\right) \quad \text{[Equation 3]}$$

$BP_{PWV}$ is a blood pressure calculated by the PWV, E is a Young's modulus, h is the thickness of a blood vessel, r is the inner radius of the blood vessel, and $\rho$ is the density of blood.

If Equation 3 is expressed simply, it may be expressed as in Equation 2.

According to various embodiments, the processor 120 may determine a calibration factor of the PWV with the blood pressure measured by the cuff hemodynamometer and the PTT value calculated by the PWV when the blood pressure is calibrated by the PWV. For example, the processor 120 may determine the constant values of $a_1$, $a_2$, $b_1$, $b_2$, and $c_1$ as correction factors in Equations 1 and 2. The processor 120 may calibrate the blood pressure value only by the PTT using the determined calibration factor. The processor 120 may extract a feature point associated with the blood pressure in a waveform in the PWA, and may calibrate the blood pressure value using the changes of the extracted feature points. The processor 120 may calibrate a blood pressure value using Equation 4 in the PWA.

$$BP_{PWA} = BP_{Base} + \Delta BP$$

$$\Delta BP = F_{CO} \times CO + F_{TP} \times TPR \quad \text{[Equation 4]}$$

According to various embodiments, the processor 120 may store the calibrated blood pressure value in a memory (e.g., the memory 130 of FIG. 1). The processor 120 may determine a calibration time point, based on a difference between the blood pressure values calculated by different calculation methods (e.g., the PWV and the PWA). Equations 1 to 4 used during an actual blood pressure calibration, $a_1$, $a_2$, $b_1$, $b_2$, $c_1$, F_CO, and F_TPRs (e.g., a calibration factor) are parameters that may slightly vary due to the change of the body of the user as time lapses. For example, the F_TPR value changes if the stiffness of a blood vessel of the user changes, and accordingly, it is necessary to perform a blood pressure calibrating operation using a cuff hemodynamometer to obtain a precise blood pressure (blood pressure value). The cuff hemodynamometer may refer, for example, to a device for calculating a blood pressure value by wrapping a cuff on a wrist of the user and applying a pressure. The precision of the blood pressure of the cuff hemodynamometer may be higher than the blood pressure measured by cuff-less hemodynamometer, such as the electronic device 101.

According to various embodiments, the processor 120 may determine a calibration time point using a difference between the blood pressure calculated by the PWV and the blood pressure calculated by the PWA. For example, if a blood pressure calibration is performed first, the calibration factor may be determined according to the body state of the user at that time. Because there is no change in the blood pressure calibration factor if the body state of the user is maintained, the blood pressure calculated by the PWV and the blood pressure calculated by the PWA may be maintained similarly. If the body state of the user changes, for example, the stiffness of a blood vessel changes, the F_TPR is influenced more significantly, and accordingly, the difference between the blood pressure calculated by the PWA and the actual blood pressure may become larger.

The processor 120 may determine a calibration time point when the difference between the blood pressure values calculated by the PWA and the PWV is more than a threshold (or deviates from a predetermined range). The processor 120 may provide guide information related to the calibration time point to the user. The guide information related to the calibration time point may be that the blood pressure (blood pressure value) calculated by the cuff hemodynamometer has to be input. For example, the input blood pressure may include a systolic blood pressure (SBP) or a diastolic blood pressure (DBP). The processor 120 may display a blood pressure input request message through a display (e.g., the display device 160), or may output a voice or vibration thorough a speaker (e.g., a sound output device 155) or vibration (e.g., the haptic module 179).

According to various embodiments, the processor 120 may determine a calibration time point based on the precision of a blood pressure. The precision of the blood pressure may change according to the user state. For example, when the user state is a static state or a sleep state, the precision of a blood pressure may be high, and when the user state is a dynamic state or an exercise state, the precision of a blood pressure may be low. The precision of a blood pressure of the sleep state may be 'high', the precision of a blood pressure of the static state may be 'middle', and the precision of a blood pressure of the dynamic state or the exercise state may be 'low'. The processor 120 may give a weight value to the precision of a blood pressure, and may determine a calibration time point based on the given weight value.

FIG. 3A is a diagram illustrating an example of calculating a blood pressure value by analyzing a pulse waveform according to various embodiments.

Referring to FIG. 3A, a pulse waveform graph 300 is illustrated. The electronic device (e.g., the electronic device 101 of FIG. 1 or the electronic device 200 of FIG. 2) according to various embodiments may acquire a waveform (e.g., the second data) of the pulse using the PPG sensor (e.g., the sensor module 211 of FIG. 2) in the PWA. A portion of the light emitted from a light source of the sensor module 211 may be absorbed by the body of the user, and another portion of the light may be reflected from the body of the user. The sensor module 211 may detect the amount of the reflected light with a detector, and may acquire a first pulse waveform 305 that repeatedly becomes larger and smaller as the heart moves. The second pulse waveform 310 may represent a waveform of a general blood pressure (e.g., an elastic artery), and the third pulse waveform 315 may represent a high blood pressure (e.g., a stiff artery). The processor (e.g., the processor 120 of FIG. 1) of the electronic device 101 may calculate a blood pressure value by analyzing the waveform of a pulse and extracting features having a high correlation with the blood pressure. For example, by comparing the second pulse waveform 310 and the third pulse waveform 315, the processor 120 may calculate a blood pressure value using a difference between the velocity of the blood (e.g., a dotted line waveform) exiting from the heart and the blood (e.g., a solid line waveform) entering the heart.

Figure 3B:
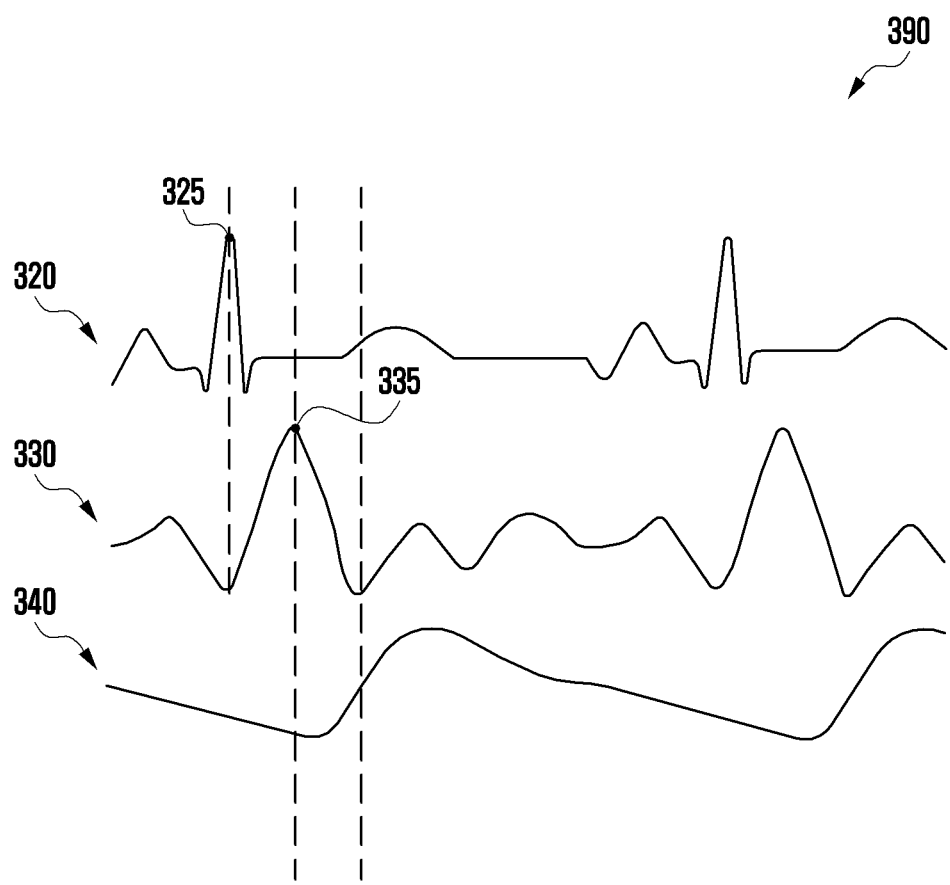
FIG. 3B is a diagram illustrating an example of calculating a blood pressure value by analyzing a blood flow velocity in an electronic device according to various embodiments.

FIG. 3B is a diagram illustrating an example of calculating a blood pressure value by analyzing a blood flow velocity in the electronic device according to various embodiments.

Referring to FIG. 3B, a blood flow velocity graph 390 is illustrated. The PWV may be classified by a pulse arrival time (PAT) method and a pulse transit time (PTT) method. The two methods may measure a blood flow time using a time point at which blood starts and a time point at which the blood arrives, and may calculate the velocity of the blood flow. The processor (e.g., the processor 120 of FIG. 1) of the electronic device (e.g., the electronic device 101 of FIG. 1 or the electronic device 200 of FIG. 2) may receive second data from the PPG sensor, may determine a pulse arrival time (PAT) value, a heart rate (HR) value, and a pulse transit time (PTT) value from the second data, and calculate a first blood pressure value BP1 and a second blood pressure value BP2 by applying the determined values to the PWV algorithm. For example, the processor 120 may estimate a blood pressure value using a proportional relationship between the calculated blood flow speed and the blood pressure. For example, the PAT method may define an R-peak 325 of a cardiogram 320 as a start time point of a blood flow, and the PTT method may define a J-peak 335 of a ballistocardiogram (BCG) 330 as a start time point of a blood flow. In a pre-ejection period (PEP) method, in the photoplethysmogram 340, a period obtained by subtracting an arrival time point of a blood flow measured by the PTT method from a start time point of a blood flow measured by the PAT method may be defined.

According to various embodiments, the start time point of a blood flow may be measured using the acceleration sensor or the gyro sensor. A fine motion generated according to a heart rate may be measured by the acceleration sensor or the gyro sensor. The start time point of a blood flow may be measured in a comfortable posture with no motion, and a clearer signal may be obtained by adhering the electronic device 101 to the chest of the user. The waveform of the motion by the heart rate is a BCG 330, and a J-peak 335 that is the largest signal is determined as a start time point of the blood flow. If the electronic device 101 includes an electrocardiograph (ECG) electrode, the R-peak 325 of the ECG 320 may be used as the start time point of the blood flow.

According to various embodiments, the electronic device 101 may measure (or calculate) a blood pressure (blood pressure value) using a camera module (e.g., the camera module 180 of FIG. 1) or an audio module (e.g., the audio module 170 of FIG. 1). For example, if the facial part of the user is photographed in a selfie mode using the camera module 180, the processor 120 may measure a change (e.g., a facial PPG) of a blood flow in a vessel according to the heart rate. It is difficult to extract a feature point for using a PWA from the waveform, the waveform may be compared with the waveform, from which a PPG is obtained from a finger, to determine the blood flow arrival time point of the PWV. The processor 120 may measure a posture of the user using the camera module 180. A phonocardiogram (PCG) that is the heart beat sound may be measured by adhering an audio microphone of the audio module 170 to the chest of the user, it may be used instead of a BCG J-peak or an ECG R-peak. The processor 120 may measure a distance between the user and the electronic device 101 using the audio module 170. The processor 120 may use the measured distance for measuring a blood pressure.

Figure 3C:
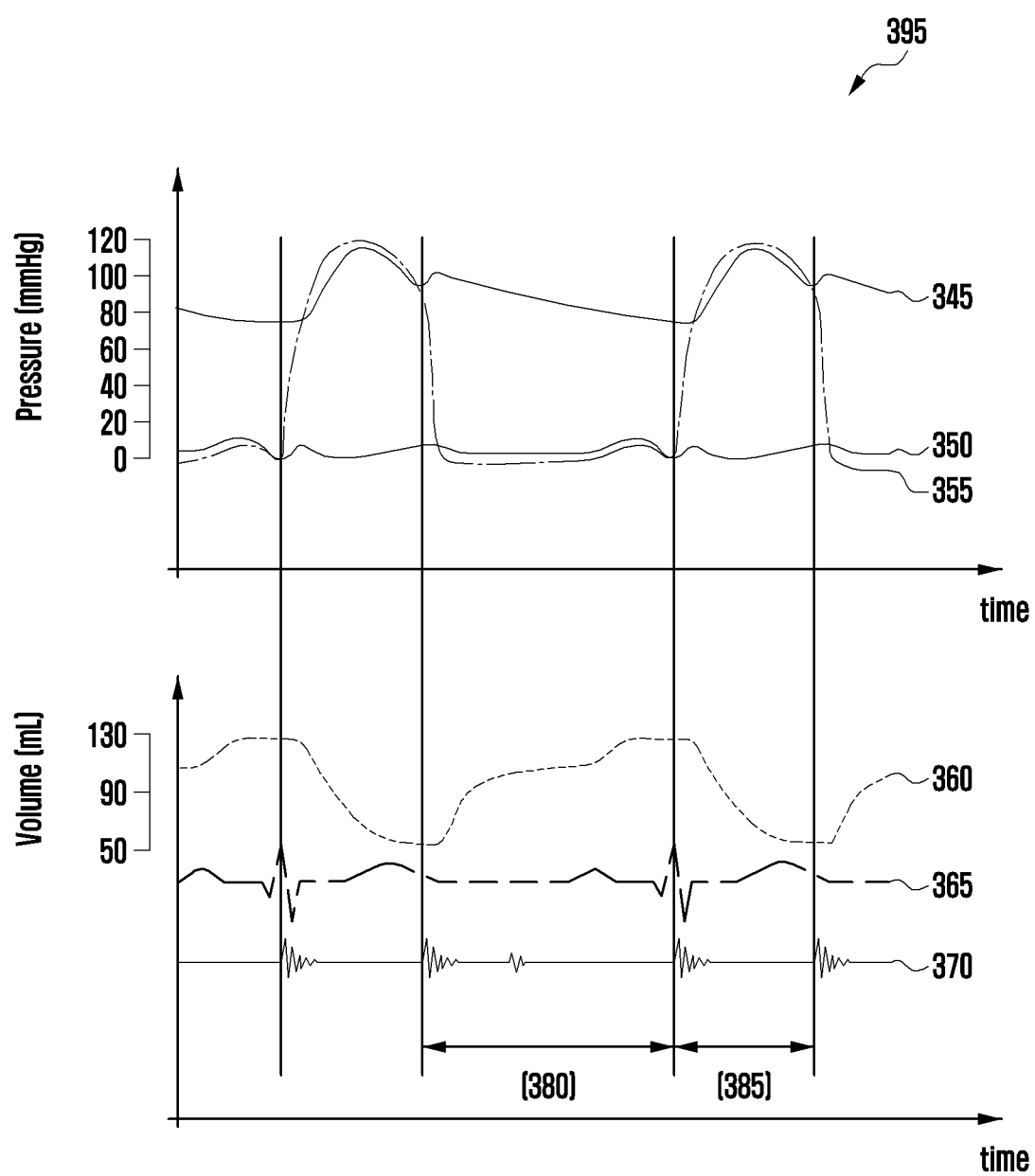
FIG. 3C is a diagram illustrating an example of calibrating a blood pressure value in an electronic device according to various embodiments.

FIG. 3C is a diagram illustrating an example of calibrating a blood pressure value in an electronic device according to various embodiments.

Referring to FIG. 3C, a blood pressure graph 395 is illustrated. The electronic device (e.g., the electronic device 101 of FIG. 1 or the electronic device 200 of FIG. 2) may calibrate the blood pressure values estimated (or calculated) by the PWV and the PWA with an actual blood pressure. For example, the processor (e.g., the processor 120 of FIG. 1) of the electronic device 101 may acquire an aortic pressure waveform 345, an atrial pressure waveform 350, and a ventricular pressure waveform 355, using sensor data (e.g., the second data) acquired from the sensor module (e.g., the sensor module 211 of FIG. 2). The processor 120 may extract a feature point associated with the blood pressure in each waveform, and may obtain a ventricular volume 360, an ECG 365, and phonocardiogram PCG 370 using a change of the extracted feature points. The processor 120 may calibrate a blood pressure value by acquiring a systolic 380 and a diastolic 385 from the photoplethysmogram 370.

The electronic device (e.g., the electronic device 101 of FIG. 1 or the electronic device 200 of FIG. 2) according to various embodiments may include a housing (e.g., the housing 210 of FIG. 2), a user interface (e.g., the display device 160 of FIG. 1 or the display 220 of FIG. 2) disposed in a first part (e.g., the first surface 210A of FIG. 2) of the housing, a photoplethysmogram (PPG) sensor (e.g., the sensor module 176 of FIG. 1 or the sensor module 211 of FIG. 2) exposed through a second part (e.g., the second surface 210B of FIG. 2) of the housing and configured to calculate a blood pressure value while contacting a portion of the body of a user, at least one sensor (e.g., the sensor module 176 of FIG. 1 or the sensor module 211 of FIG. 2), a wireless communication circuit (e.g., the wireless communication module 192 of FIG. 1) located in the interior of the housing, a processor (e.g., the processor 120 of FIG. 1) located in the interior of the housing and operatively connected to the user interface, the PPG sensor, the at least one sensor, and the wireless communication circuit, and a memory (e.g., the memory 130 of FIG. 1) operatively connected to the processor, wherein the memory stores instructions that, when executed by the processor, control the electronic device to: receive first data from the at least one sensor, receive second data from the PPG sensor at least partially based on the received first data, determine a pulse arrival time (PAT) value, a heart rate (HR) value, and a pulse transit time (PTT) value from the second data, calculate a first blood pressure value BP1 and a second blood pressure value BP2 by applying the determined values to pulse wave velocity PWV algorithms of Equations 1 and 2, wherein $BP1 \cong a_1 PAT + b_1 HR + c_1$ ... Equation 1 $BP2 \cong a_2 \ln(PTT) + b_2$ ... Equation 2, wherein in Equations 1 and 2, $a_1$, $a_2$, $b_1$, $b_2$, and $c_1$ may be constant values for matching blood pressure values measured during calibration with blood pressure values measured by a cuff hemodynamometer, determine a calibration time point at least partially based on a difference between the first blood pressure value and the second blood pressure value, and provide information related to the calibration time point through the user interface, at least partially based on the determination.

The instructions may, when executed by the processor, control the electronic device to, when the first data is a selected threshold value or less, receive second data from the PPG sensor.

The at least one sensor may include at least one of an acceleration sensor, a proximity sensor, a temperature sensor, or an iris sensor.

The instructions may, when executed by the processor, control the electronic device to store the calculated blood pressure value in the memory at least partially based on the difference between the first blood pressure value and the second blood pressure value.

The electronic device may be a wearable device.

The instructions may, when executed by the processor, control the electronic device to receive a third blood pressure value input from a user in response to the informed information, and store the input third blood pressure value in the memory.

The instructions may, when executed by the processor, control the electronic device to guide a precision of blood pressure until the third blood pressure value is input.

The instructions may, when executed by the processor, control the electronic device to determine the constant values at least partially based on the third blood pressure value, and calculate the first blood pressure value and the second blood pressure value at least partially based on the determined constant value.

The electronic device (e.g., the electronic device 101 of FIG. 1 or the electronic device 201 of FIG. 2) may include a housing (e.g., the housing 210 of FIG. 2), a user interface (e.g., the display device 160 of FIG. 1 or the display 220 of FIG. 2) disposed in a first part (e.g., the first surface 210A of FIG. 2) of the housing, a PPG sensor (e.g., the sensor module 176 of FIG. 1 or the sensor module 211 of FIG. 2) exposed through a second part (e.g., the second surface 210B of FIG. 2) of the housing, and configured to calculate a blood pressure value while contacting a portion of a body of a user, a wireless communication circuit (e.g., the wireless communication module 192 of FIG. 1) located in the interior of the housing, a processor (e.g., the processor 120 of FIG. 1) located in the interior of the housing, and operatively connected to the user interface, the PPG sensor, and the wireless communication circuit, and a memory (e.g., the memory 130 of FIG. 1) operatively connected to the processor, wherein the memory stores instructions that, when executed by the processor, control the electronic device to receive data from the PPG sensor, determine a PAT value, an HR value, and a PTT value from the data, calculate a first blood pressure value and a second blood pressure value by applying the determined values to a first pulse wave velocity (PWV) algorithm using the PAT value and the HR value and a second PWV algorithm using the PTT value, determine whether a calibration is necessary, at least partially based on a difference between the first blood pressure value and the second blood pressure value, and provide information related to the calibration through the user interface, at least partially based on the determination.

The instructions may, when executed by the processor, control the electronic device to determine one or more parameters from the data, and calculate the first blood pressure value and the second blood pressure value at least partially based on, among the determined at least one parameters, at least two parameters which do not overlap each other, and a correction factor.

The instructions may, when executed by the processor, control the electronic device to guide a precision of blood pressure until the third blood pressure value is input.

The electronic device (e.g., the electronic device 101 of FIG. 1 or the electronic device 201 of FIG. 2) according to various embodiments may include a housing (e.g., the housing 210 of FIG. 2), a user interface (e.g., the display device 160 of FIG. 1 or the display 220 of FIG. 2) disposed in a first part (e.g., the first surface 210A of FIG. 2) of the housing, a PPG sensor (e.g., the sensor module 176 of FIG. 1 or the sensor module 211 of FIG. 2) exposed through a second part (e.g., the second surface 210B of FIG. 2) of the housing, and configured to calculate a blood pressure value while contacting a portion of a body of a user, a wireless communication circuit (e.g., the wireless communication module 192 of FIG. 1) located in the interior of the housing, a processor (e.g., the processor 120 of FIG. 1) located in the interior of the housing and operatively connected to the user interface, the PPG sensor, and the wireless communication circuit, and a memory (e.g., the memory 130 of FIG. 1) operatively connected to the processor, wherein the memory stores instructions that, when executed by the processor, control the electronic device to receive data from the PPG sensor, determine a PTT value and a cardiac output (CO) value, and a total peripheral resistance (TPR) value from the data, calculate a first blood pressure value and a second blood pressure by applying the determined values to a first pulse wave velocity (PWV) algorithm using the PTT value and a second PWA algorithm using the CO value and the TPR value, determine whether a calibration is necessary, at least partially based on a difference between the first blood pressure value and the second blood pressure value, and provide information related to the calibration through the user interface, at least partially based on the determination.

The instructions may, when executed by the processor, control the electronic device to detect a user state using sensor data acquired from the at least one sensor, in a case in which the user state is a preset state, calculate a first blood pressure value and a second blood pressure value, and in a case in which a difference between the first blood pressure value and the second blood pressure value is more than a threshold, determine whether the calibration is necessary.

The instructions may, when executed by the processor, control the electronic device to, in a case in which a difference between the first blood pressure value and the second blood pressure value is more than a threshold, detect the user state, and in a case in which the user state is a preset state, recalculate a first blood pressure value and a second blood pressure value.

The instructions may, when executed by the processor, control the electronic device to, in a case in which the user state is not the preset state, make a request for an input of a third blood pressure value.

The user state may include at least one of a static state, a dynamic state, a sleep state, or an exercise state, and the preset state may be the static state or the sleep state.

The instructions may, when executed by the processor, control the electronic device to delete a blood pressure value stored in the memory, in response to input of a third pressure blood pressure value, and store the third pressure blood pressure value, and recalculate the first blood pressure value and the second blood pressure value at least partially based on the stored third blood pressure value.

The instructions may, when executed by the processor, control the electronic device to, in a case in which a motion of the user corresponds to a first condition, calculate the first blood pressure value and the second blood pressure value with any one of the first PWV algorithm or the second PWA algorithm.

The instructions may, when executed by the processor, control the electronic device to, in a case in which a motion of the user corresponds to a second condition, calculate a fourth blood pressure value by correcting the first blood pressure value calculated by the first PWV algorithm and the second blood pressure value calculated by the second PWA algorithm.

The instructions may, when executed by the processor, control the electronic device to, in a case in which a motion of the user corresponds to a third condition, determine whether a calibration is necessary, using the first blood pressure value calculated by the first PWV algorithm and the second blood pressure value calculated by the second PWV algorithm.

FIG. 4 is a flowchart 400 illustrating an example method of operating an electronic device according to various embodiments.

Referring to FIG. 4, in operation 401, the processor (e.g., the processor 120 of FIG. 1) of the electronic device (e.g., the electronic device 101 of FIG. 1 or the electronic device 200 of FIG. 2) according to various embodiments may receive first data from at least one sensor (e.g., the sensor module 176 of FIG. 1 or the sensor module 211 of FIG. 2). The at least one sensor may include at least one of an acceleration sensor, a proximity sensor, a temperature sensor, an iris sensor, or a PPG sensor. The first data may be sensor data detected (or measured) by the at least one sensor.

In operation 403, the processor 120 may receive second data from the PPG sensor (e.g., the sensor module 176 of FIG. 1 or the sensor module 211 of FIG. 2), at least partially based on the received first data. The PPG sensor may be exposed though a second part (e.g., the second part 110B) of the housing 210 of the electronic device 200, and may be configured to calculate a blood pressure value while contacting a portion of the body of the user. The processor 120 may determine a pulse arrival time (PAT) value, a heart rate (HR) value, and a pulse transit time (PTT) value from the second data. The processor 120 may receive second data from the PPG sensor when the first data is a selected threshold value or less.

In operation 405, the processor 120 may determine a PAT value, an HR value, and a PTT value from the second data. The processor 120 may determine the HR value using the second data. The processor 120 may calculate the start time point of a blood flow from the second data, and may determine a PAT value, an HR value, and a PTT value by calculating the arrival time point of the blood flow from the first data. The processor 120 may calculate a PAT value using an ECG waveform, and may determine a PTT value using a BCG waveform (for example, see FIGS. 3A to 3C).

In operation 407, the processor 120 may calculate a first blood pressure value BP1 and a second blood pressure value BP2 by applying the determined values to the pulse wave velocity (PWV) algorithm. The processor 120 may calculate a blood pressure value by measuring a blood flow time using a time point at which blood starts and a time point at which the blood arrives, and calculating the velocity of the blood flow. The processor 120 may calculate the first blood pressure value and the second blood pressure value by applying Equations 1 and 2 to the PWV algorithm.

According to various embodiments, the processor 120 may determine a PTT value and blood pressure features from the second data, and may calculate the first blood pressure value and the second blood pressure value by applying the determined values to a first PWV algorithm using the PTT value and a second PWA algorithm using the values of the blood pressure features.

In operation 409, the processor 120 may determine a calibration time point based at least in part on a difference between the first blood pressure value and the second blood pressure value. The processor 120 may store the calculated blood pressure value in the memory (e.g., the memory 130 of FIG. 1) at least partially based on the difference between the first blood pressure value and the second blood pressure value. If the equations for calculating the blood pressure are different, the parameter used to calculate the blood pressure value also becomes different, and thus the blood pressure value corresponding to a result value may become different. The processor 120 may determine that the blood pressure is normally calculated and calibrated when a difference between the first blood pressure value and the second blood pressure value is less than a threshold. The processor 120 may store the calibrated blood pressure value in the memory 130 when the difference between the blood pressures is less than the threshold. The processor 120 also may provide the calibrated blood pressure value to the user. The processor 120 may display a value, a level, or a graph for the blood pressure through the display device 160. The processor 120 may determine that a calibration of blood pressure is necessary when the difference between the blood pressures is more than the threshold. The processor 120 may determine a calibration time point when the difference between the blood pressures is more than the threshold.

According to various embodiments, the processor 120 may determine a blood pressure calculating method or equation based on the user state, and may calculate a blood pressure value based on the determined blood pressure calculating method or equation. The user state also may include at least one of a static state, a dynamic state, a sleep state, or an exercise state. For example, the processor 120 may determine whether the blood pressure value will be calculated by the PWA or the blood pressure value will be calculated by the PWV, based on the user state. The processor 120 may calculate the blood pressure value by the PWA when the user state is a static state, and may calculate the blood pressure value by the PWV when the user state is a dynamic state.

In operation 411, the processor 120 may provide guide information related to the calibration time point through the user interface (e.g., the display device 160 of FIG. 1 or the display 220 of FIG. 2) at least partially based on the determination. The processor 120 may display a user interface including a guide message through the user interface, and may output a voice or vibration through a speaker (e.g., the sound output device 155) or vibration (e.g., the haptic module 179).

The processor 120 may provide a guide for inputting the blood pressure (blood pressure value) measured by the cuff hemodynamometer to the user to more precisely measure a blood pressure as the guide information. The input blood pressure may include a systolic blood pressure (SBP) and a diastolic blood pressure (DBP).

Figure 5A:
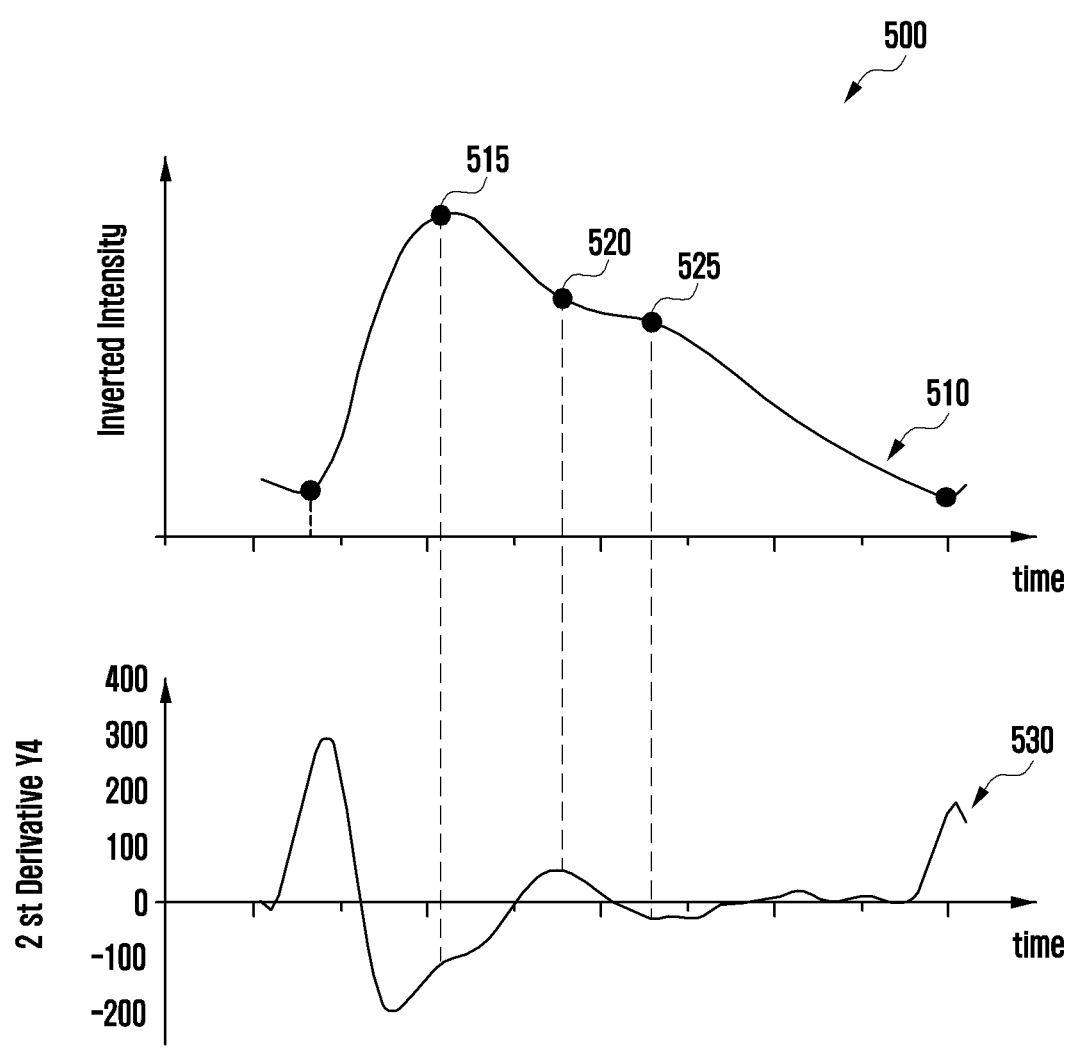
FIG. 5A is a diagram illustrating an example of calculating a blood pressure value in an electronic device according to various embodiments.
Figure 5B:
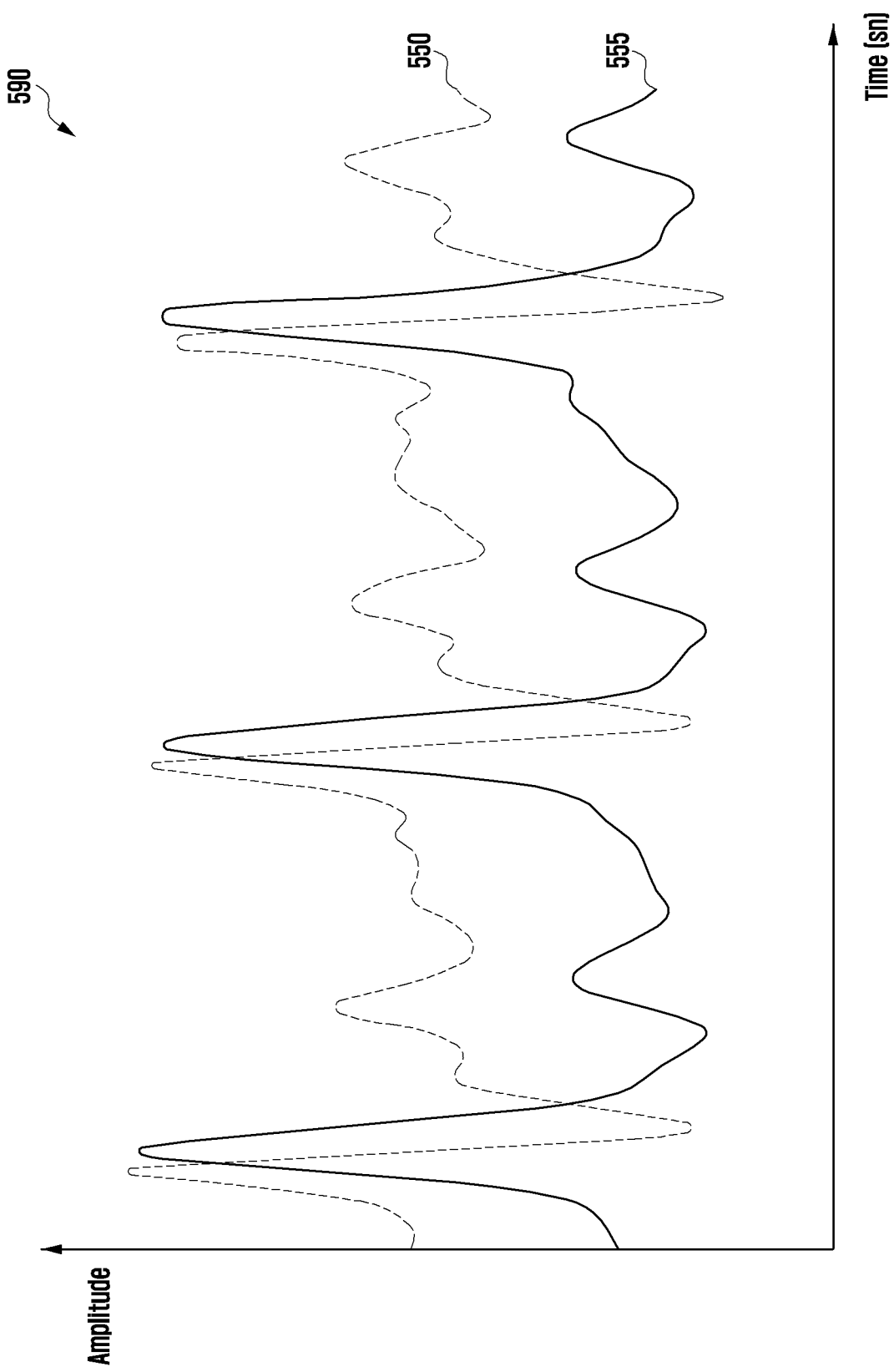
FIG. 5B is a diagram illustrating an example of calculating a blood pressure value in an electronic device according to various embodiments.
Figure 5C:
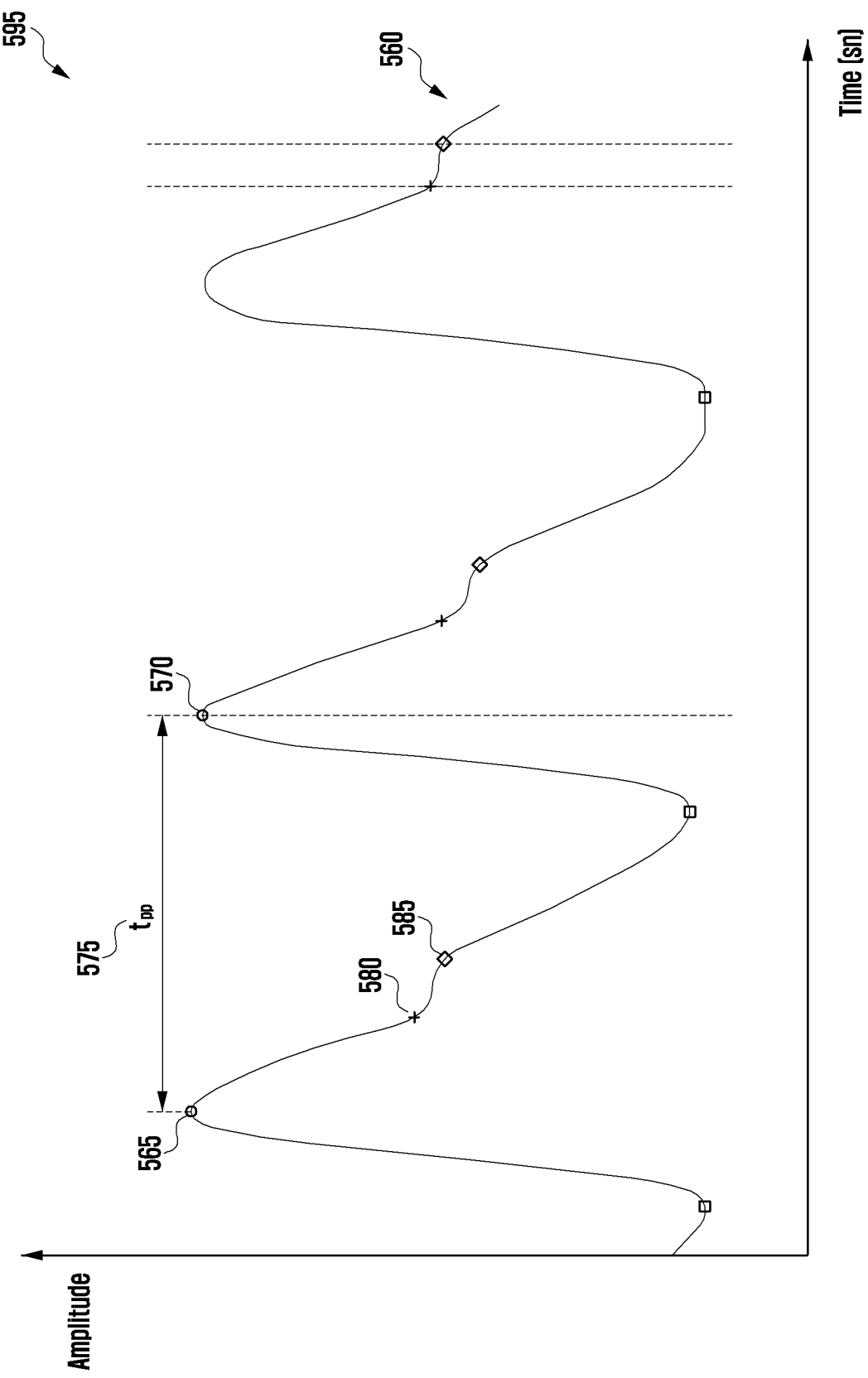
FIG. 5C is an example pulse signal graph according to various embodiments.

FIG. 5A is a diagram illustrating an example of calculating a blood pressure value in an electronic device according to various embodiments, and FIG. 5B is a diagram illustrating an example of calculating a blood pressure value in an electronic device according to various embodiments. FIG. 5C is a pulse signal graph according to various embodiments.

Referring to FIG. 5A, a graph 500 related to a pulse waveform is illustrated. The processor (e.g., the processor 120 of FIG. 1) of the electronic device (e.g., the electronic device 101 of FIG. 1 or the electronic device 200 of FIG. 2) may measure the heart rate (or the pulse) using the sensor data (e.g., the second data) acquired by the PPG sensor (e.g., the sensor module 176 of FIG. 1 or the sensor module 211 of FIG. 2). The processor 120 may acquire a pulse from the second data, and may acquire an inverted signal 510 by inverting the acquired pulse. The processor 120 may acquire a differential signal 530 by differentiating the inverted signal 510, may extract feature points of the inverted signal 510 and the differential signal 530, and may acquire a systolic 515, a diastolic 525, and a diastolic notch 520 by matching the extracted feature points. The atria and the ventricles of the heart are not contracted or released perfectly at the same time. A state or a timing in which the atria or the ventricles are contracted may be referred to as a systolic 515. The systolic 515 may refer, for example, to the heart sending blood to the vascular system, and if a ventricular pressure becomes an aortic pressure or more, the aortic valve is opened to discharge blood. If the ventricular pressure becomes lower than the aortic pressure, the aortic valve is closed, and then, a state in which the aortic pressure instantaneously increases and decreases again may be a diastolic notch 520. The diastolic 525 may refer, for example, to the ventricles being expanded while the atria are contracted, and then, the blood may be introduced from the atria to the ventricles.

Referring to FIG. 5B, a differentiation graph 590 for pulses is illustrated. The processor 120 may acquire a first differential signal 550 obtained by differentiating a pulse one time, and a second differential signal 555 obtained by differentiating a pulse two times. The processor 120 may extract a feature point from the first differential signal 550 or the second differential signal 555, and may calculate a blood pressure value using the extracted feature point.

Referring to FIG. 5C, a pulse signal graph 595 is illustrated. The processor 120 may detect a pulse signal 560 according to a blood flow of the heart. The pulse may include an augmentation index (AI), an augmentation point (AP), and a dicrotic notch. The processor 120 may calculate a blood pressure value using a CO related to a blood pressure, a TPR, and a feature point of a blood pressure having a high degree of association with the stiffness of a blood vessel. The processor 120 may determine a PTT value and a blood pressure feature value from data (e.g., the second data) acquired by the PPG sensor. The processor 120 may calculate a first blood pressure value and a second blood pressure value by applying the determined values to a first PWV algorithm using the PTT value and a second PWA algorithm using the blood pressure feature value. The processor 120 may acquire a systolic (e.g., a first systolic 565 or a second systolic 570), a diastolic notch 580, and a diastolic 585 from the pulse signal 560. The processor 120 may measure a time period 575 between the first systolic 565 and the second systolic 570 to use the measured time period 575 in calculating a blood pressure.

Figure 6:
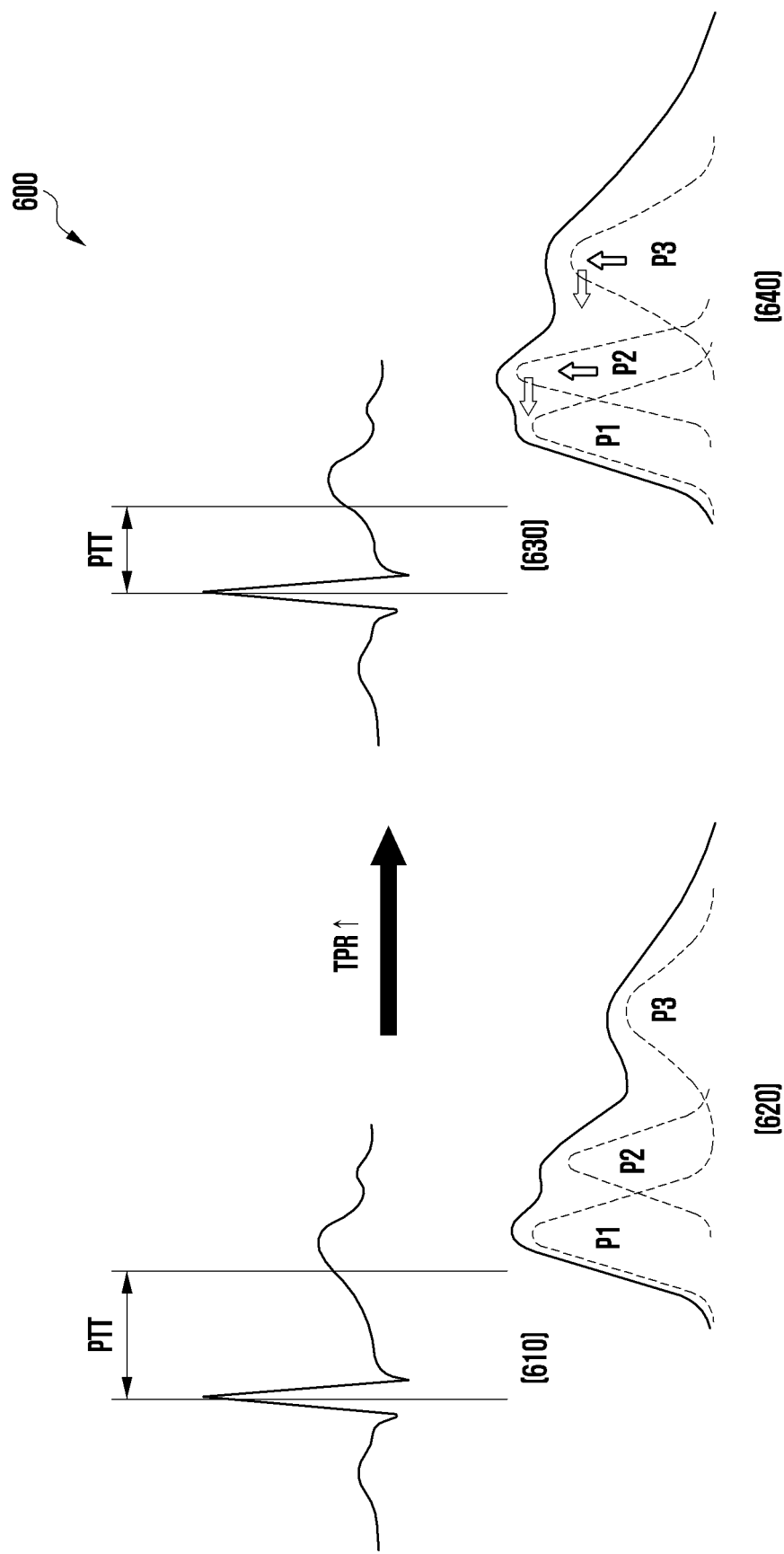
FIG. 6 is a diagram illustrating an example of changing a pulse according to various embodiments.

FIG. 6 is a diagram illustrating an example 600 of changing a pulse according to various embodiments.

The processor (e.g., the processor 120 of FIG. 1) of the electronic device (e.g., the electronic device 101 of FIG. 1 or the electronic device 200 of FIG. 2) may acquire a first cardiogram signal 610 and a first pulse signal 620 using the sensor data (e.g., the second data) acquired by the PPG sensor (e.g., the sensor module 176 of FIG. 1 or the sensor module 211 of FIG. 2), and may calculate a blood pressure value using the first cardiogram 610 or the first pulse 620. The blood pressure may vary according to the body change or state of the user. For example, a total peripheral resistance TPR may change as a blood vessel stiffens. After the TPR changes, the processor 120 may acquire a second cardiogram 630 and a second pulse 640. When the first pulse 620 and the second pulse 640 are compared, 'P2' that is a reflected wave in the second pulse 640 is reflected on the waveform more promptly and the entire waveform of the pulse may change. When the processor 120 uses an F_TPR used when the first cardiogram 610 or the first pulse 620 is measured to acquire the second cardiogram 630 and the second pulse 640, an error may occur in calculating a blood pressure. If the processor 120 calculates a blood pressure value using the previous used calibration factor as it is after the vascular characteristics of the user change, the calculated blood pressure value may be different from the actual blood pressure value. The processor 120 may determine a blood pressure calculating method based on the user state. For example, the processor 120 may calculate a blood pressure value by the PWV when the blood pressure value is calculated using an existing calibration factor (e.g., F_(PWV_α), F_(PWV_β)).

Figure 7:
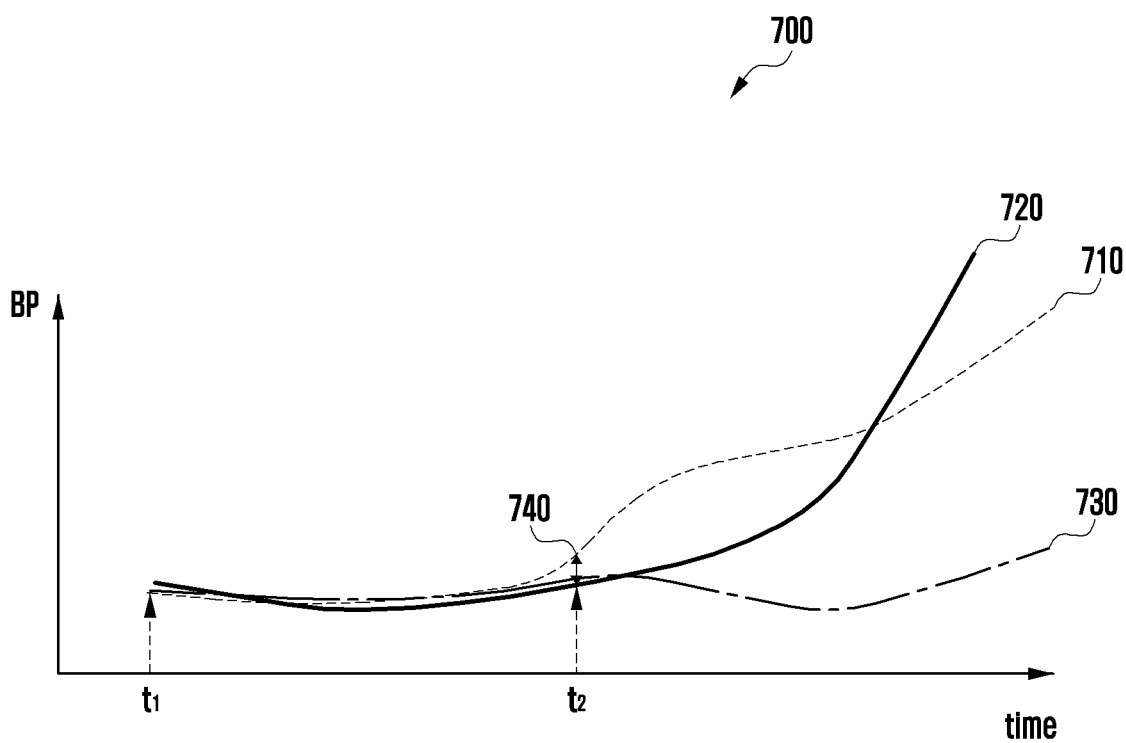
FIG. 7 is a diagram illustrating an example in which a difference between blood pressure values deviates from a threshold according to various embodiments.

FIG. 7 is a diagram illustrating an example 700 in which a difference between blood pressure values deviates from a threshold according to various embodiments.

Referring to FIG. 7, the processor (e.g., the processor 120 of FIG. 1) of the electronic device (e.g., the electronic device 101 of FIG. 1 or the electronic device 200 of FIG. 2) may calculate a blood pressure value in various methods using a blood pressure value input at t1. For example, the first blood pressure value 710 may be calculated using the PWA, and the second blood pressure value 720 may be calculated using the PWV. The third blood pressure value 730 may be calculated using any one of the PWA or the PWV using a parameter that is different from the parameter used when the first blood pressure value 710 or the second blood pressure value 720 is calculated. If there is no change in the body of the user after t1, the first to third blood pressure values 710 to 730 may show a similar aspect. If there is a change in the body of the user after t2, the first to third blood pressure values 710 to 730 may show different aspects. The processor 120 may guide a calibration of a blood pressure to the user when the difference between the first to third blood pressure values 710 to 730 is larger than the threshold 740. A specific value may be used as the threshold, a specific ratio may be used as the threshold, and a value personalized for the user may be used as the threshold.

If there is no difference between the first to third blood pressure values 710 to 730, the processor 120 may determine a current blood pressure value of the user using the first to third blood pressure values 710 to 730 without having to input a new blood pressure value, and may store the determined blood pressure value in the memory (e.g., the memory 130 of FIG. 1). The processor 120 may give weight values to the first to third blood pressure values 710 to 730 based on the user state, and may determine a current blood pressure value using the first to third blood pressure values 710 to 730 having the given weight values.

Figure 8:
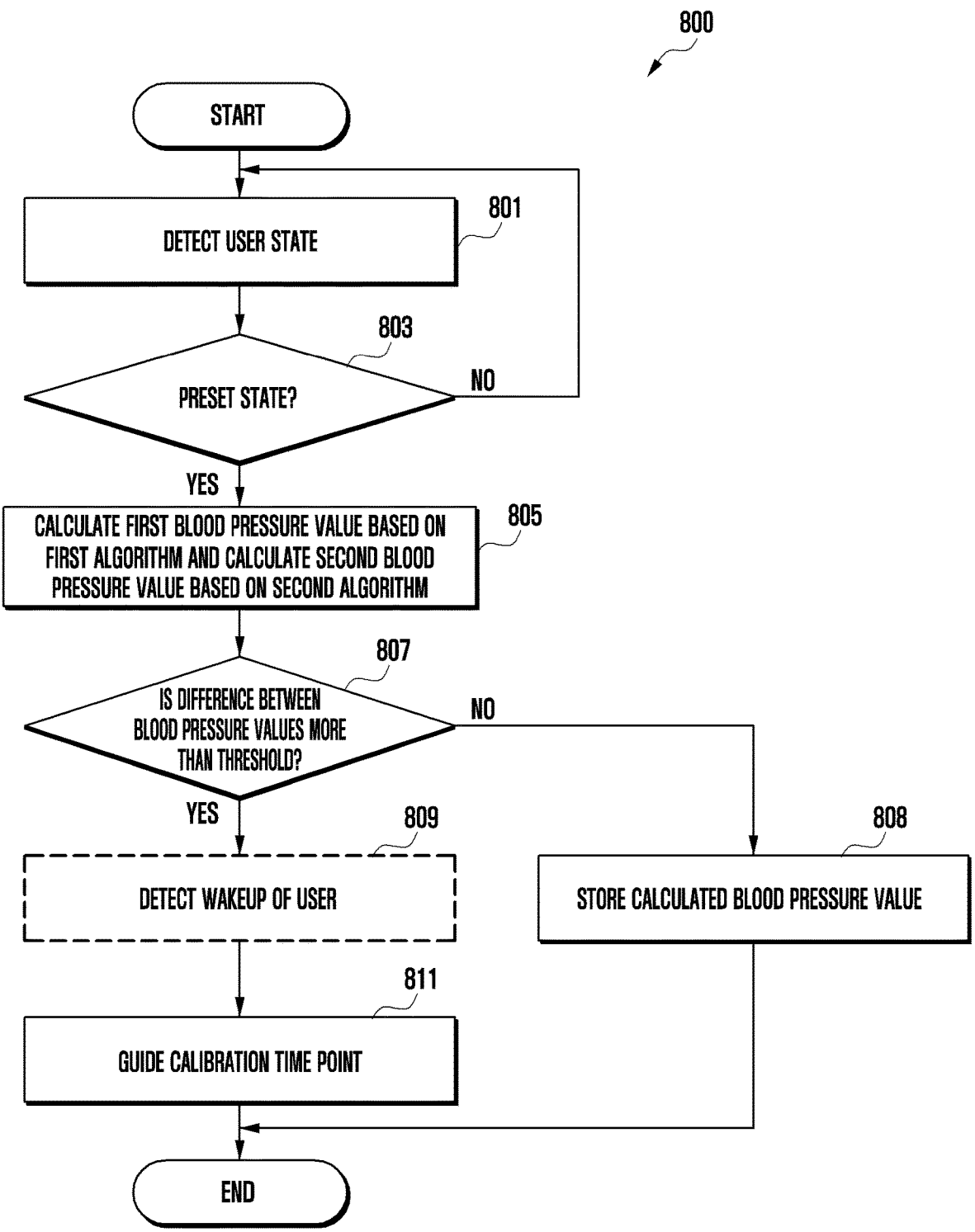
FIG. 8 is a flowchart illustrating a example method of guiding a blood pressure calibration time point in an electronic device according to various embodiments.

FIG. 8 is a flowchart 800 illustrating an example method of guiding a calibration time point in an electronic device according to various embodiments.

Referring to FIG. 8, in operation 801, the processor (e.g., the processor 120 of FIG. 1) of the electronic device (e.g., the electronic device 101 of FIG. 1 or the electronic device 200 of FIG. 2) according to various embodiments may detect (or recognize) a user state. The processor 120 may detect a user state using sensor data (e.g., the first data) acquired by at least one sensor (e.g., the sensor module 176 of FIG. 1 or the sensor module 211 of FIG. 2). The user state may be classified into a state having a motion and a state without a motion. The user state also may be classified into a static state, a dynamic state, or a sleep state. The user state also may include at least one of a static state, a dynamic state, a sleep state, or an exercise state. In detail, the static state may be classified into a state in which the user is seated and there is almost no motion, a state in which there is a slow and moderate motion, and a state in which the user eats meal. The dynamic state may be a state in which there is a motion that is larger than that of the static state but the motion is smaller than that of the exercise state. The exercise state may be classified into anaerobic exercise and aerobic exercise or may be classified into one or more levels according to a heart rate. The sleep state may be classified into snoring, apnea, tossing and turning, and an REM/NREM state.

According to various embodiments, the processor 120 may give different weight values to the PTT and the PWA according to the user state. The weight value may be variously determined from 0 to 1. For example, when the current heart rate is very high, the feature point extracted from the pulse signal using the PWA may not appear clearly. The processor 120 may give a weight value of 1 to the feature point extracted using the PWV, and may give a weight value of 0 to the feature point extracted using the PWA.

In operation 803, the processor 120 may determine whether the user state is a preset state. The preset state may include a static state or a sleep state. The processor 120 may perform operation 805 when the user state is a preset state (e.g., YES), and may return to operation 801 when the user state is not the preset state (e.g., NO). The processor 120 may return to operation 801 to periodically or selectively detect the user state, and when the user state is a state in which it is possible to calculate a blood pressure, may calculate the blood pressure value.

According to various embodiments, in the processor 120, a possibility in which the blood pressure measured in a state (e.g., a dynamic state or an exercise state) with a motion is different from the actual blood pressure may be high. The blood pressure calculated not by a cuff hemodynamometer but by the electronic device 101 in a state with a motion may not be trustworthy. When the blood pressure is calculated in a comfortable and stable state in which there is no motion, precision may be high. For example, in order to extract a blood pressure value by the PWA or the PWV, the user state has to be maintained in a state, such as a static state or a sleep state, in which there is no motion. When the user is sleeping, there is almost no motion except for temporary tossing and turning. If a motion during a sleep is measured by an acceleration sensor, the variance of the acceleration signal is maintained at 40 mg or less, and the value is very small, and may not be applied to a biometric signal obtained by measuring a pulse/a cardiogram/a ballistocardiogram as motion noise. In the static state, the variance is maintained at 200 mg or less if a motion corresponding to being seated on a chair and doing a job comfortably, for example, typing on a keyboard, and the value may not greatly influence finding a peak of the pulse signal.

When the user state is a preset state (e.g., YES), in operation 805, the processor 120 may calculate a first blood pressure value based on a first algorithm, and may calculate a second blood pressure value based on a second algorithm. The first algorithm may, for example, be the PWA, and the second algorithm may, for example, be the PWV. For example, the processor 120 may determine the PTT value and the values of the blood pressure features using the data acquired by the PPG sensor, may calculate the first blood pressure value using the PWV algorithm using the PTT value, and may calculate the second blood pressure value by applying the PWA algorithm using the blood pressure feature values. The first algorithm may calculate a blood pressure value with first to third parameters, among a plurality of parameters for calculating a blood pressure value, and the second algorithm may calculate a blood pressure value with fourth to eighth parameters. For example, the processor 120 may determine a PAT value, an HR value, and a PTT value using the data acquired by the PPG sensor, and may calculate a blood pressure value by applying the determined values to the first PWV algorithm using the PAT value and the HR value (e.g., by applying the determined values to Equation 1). The processor 120 may calculate a blood pressure value by applying the determined values to the second PWV algorithm using the PTT value (e.g., by applying the determined values to Equation 2). If the parameter is changed, the applied equation may be changed.

Although FIG. 8 illustrates that two blood pressure values are calculated, more than two blood pressure values may be calculated with algorithms that do not overlap each other.

According to various embodiments, the processor 120 may determine a blood pressure calculating method based on the user state. For example, the processor 120 may calculate the blood pressure value by the PWA when the user state is a sleep state, and may calculate the blood pressure value by the PWV when the user state is a static state. The processor 120 may calculate a blood pressure value through any one method of the PWA or the PWV when the user state is a sleep state, and may calculate the blood pressure value using the PWA and the PWV when the user state is a static state.

According to various embodiments, before operation 801, the blood pressure value calculated in the cuff hemodynamometer may be stored in the memory (e.g., the memory 130 of FIG. 1). The processor 120 may calibrate the blood pressure value calculated using the stored blood pressure value. The processor 120 may determine a calibration factor for a blood pressure calibration using the stored blood pressure value. The calibration factor is a constant value, and may be applied to an algorithm used to calculate the blood pressure value and may be applied to a calibration algorithm after the calculation of the blood pressure. The processor 120 may calibrate the blood pressure value calculated using the calibration factor. Because a parameter related to a blood pressure will maintain the same value as in the calibration if there is no change in the body of the user, for example, no change in the stiffness of a blood vessel, the viscosity of the blood, and the thickness of the blood vessel, the blood pressure values calculated using the parameters will show similar values. For example, because the blood pressure value obtained using the PWV is calculated through the speed of blood, it may be greatly influenced by the stiffness of a blood vessel, the viscosity of the blood, and the thickness of the blood vessel.

In operation 807, the processor 120 may determine whether the difference between the blood pressure values is more (e.g., greater) than the threshold. If the body state of the user changes differently from when the blood pressure calibration is made, the calibration factor obtained through the blood pressure calibration also may change. If the blood pressure value is calculated using an existing calibration factor even after the body of the user changes, the calculated blood pressure value is different from the actual blood pressure value, and the difference may show different aspects according to an algorithm for calculating a blood pressure value. The processor 120 may perform operation 809 when the difference between the blood pressure values is more than the threshold (e.g., YES), and may perform operation 808 when the difference between the blood pressure values is less than or equal to the threshold value (e.g., NO).

When the difference between the blood pressure values is less than or equal to the threshold (e.g., NO), in operation 808, the processor 120 may store the calculated blood pressure value in the memory 130. The processor 120 may provide the calculated blood pressure value to the user. The processor 120 may display a value, a level, or a graph for the blood pressure through the display device 160 (or the display 220 of FIG. 2).

When the difference between the blood pressure values is more than the threshold (e.g., YES), in operation 809, the processor 120 may detect a wakeup of the user. Operation 809 may be performed when the user state detected in operation 801 is a sleep state. The processor 120 may guide a blood pressure calibration if the user wakes up without a display through the display or an alarm through a speaker while the user is sleeping. For example, the processor 120 may determine a change of the acceleration data or the gyro data, and may determine that the user woke up when there is a change. The processor 120 may determine whether there is a change of the sensing data acquired from an external device interworking with the electronic device 101, and may determine that the user woke up if there is a change. The processor 120 may determine whether a wakeup alarm is set in the electronic device 101, and may determine that the user woke up after the wakeup alarm has sounded when the wakeup alarm is set. Operation 809 is performed when the user state is a sleep state, and may be omitted when the user state is not a sleep state.

In operation 811, the processor 120 may guide a blood pressure calibration. The processor 120 may guide a calibration time point when the difference between the blood pressures is more than the threshold. The processor 120 may provide a guide for inputting a blood pressure value measured by a cuff hemodynamometer to the user to calculate the blood pressure more precisely.

Figure 9:
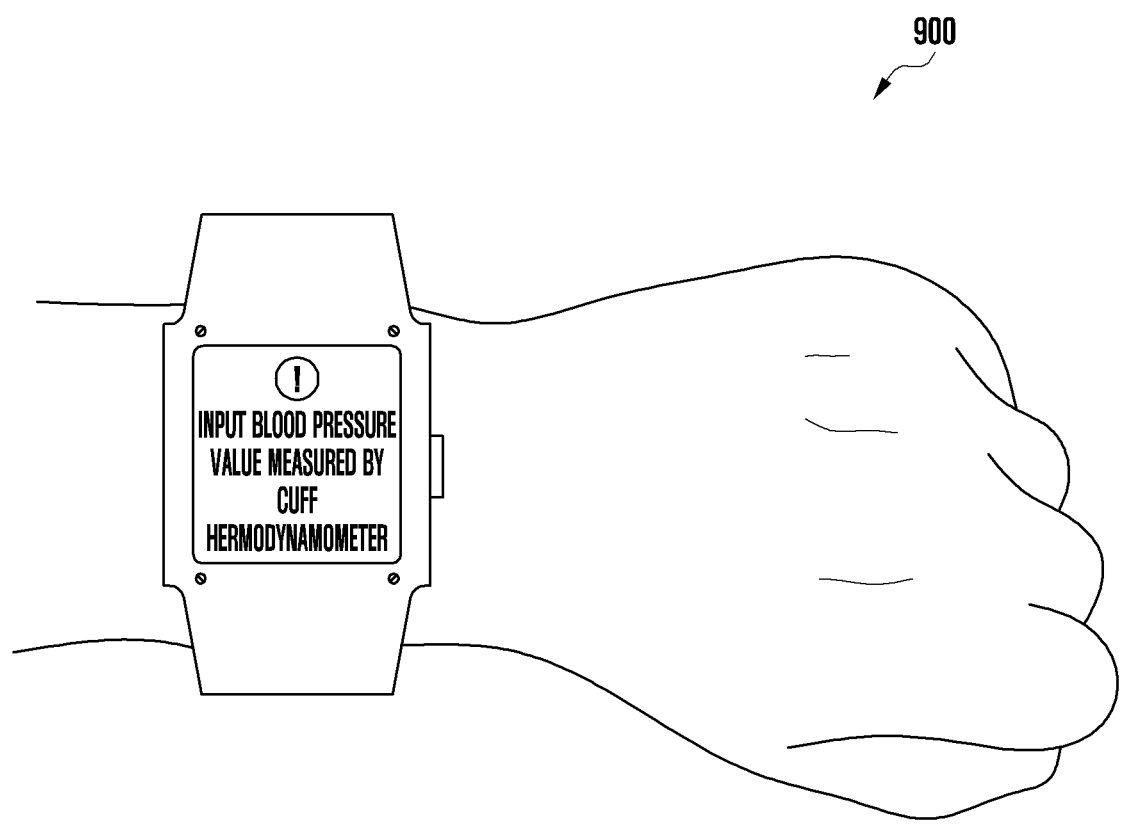
FIG. 9 is a diagram illustrating an example of a user interface that guides a blood pressure calibration in an electronic device according to various embodiments.

FIG. 9 is a diagram illustrating an example of a user interface 900 that guides a blood pressure calibration in an electronic device according to various embodiments.

Referring to FIG. 9, the processor (e.g., the processor 120 of FIG. 1) of the electronic device (e.g., the electronic device 101 of FIG. 1 or the electronic device 200 of FIG. 2) according to various embodiments may display a blood pressure input request message on the display (e.g., the display device 160 of FIG. 1 or the display device 220 of FIG. 2). The blood pressure input request message may include at least one of a text (e.g., "Input the blood pressure value measured by cuff hemodynamometer."), an image (e.g., a warning icon) or a video. The processor 120 may output a voice or vibration through a speaker (e.g., the sound output device 155) or vibration (e.g., the haptic module 179) when the blood pressure input request message is displayed.

Figure 10:
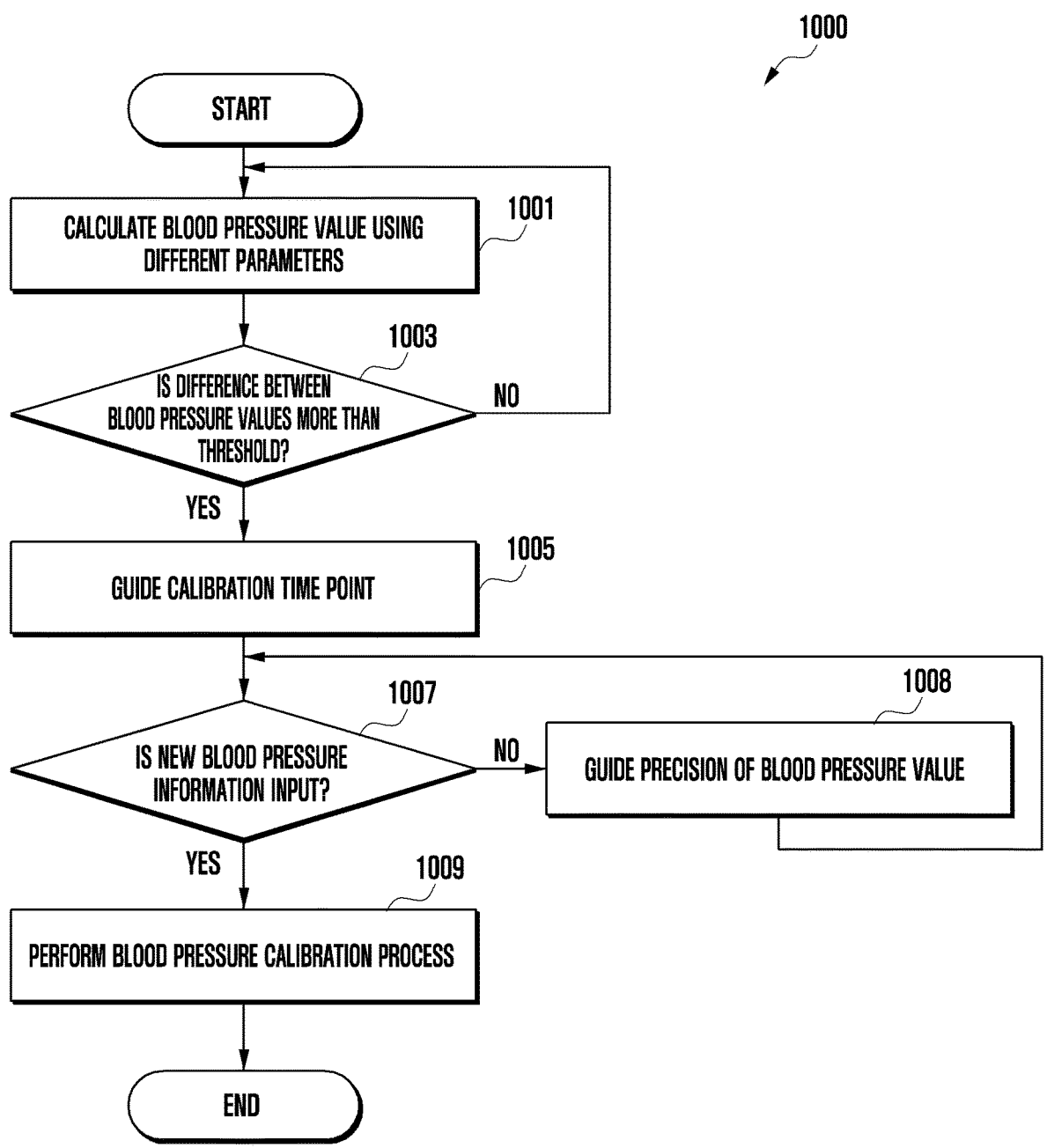
FIG. 10 is a flowchart illustrating an example method of guiding a blood pressure calibration time point of an electronic device according to various embodiments.
Figure 11:
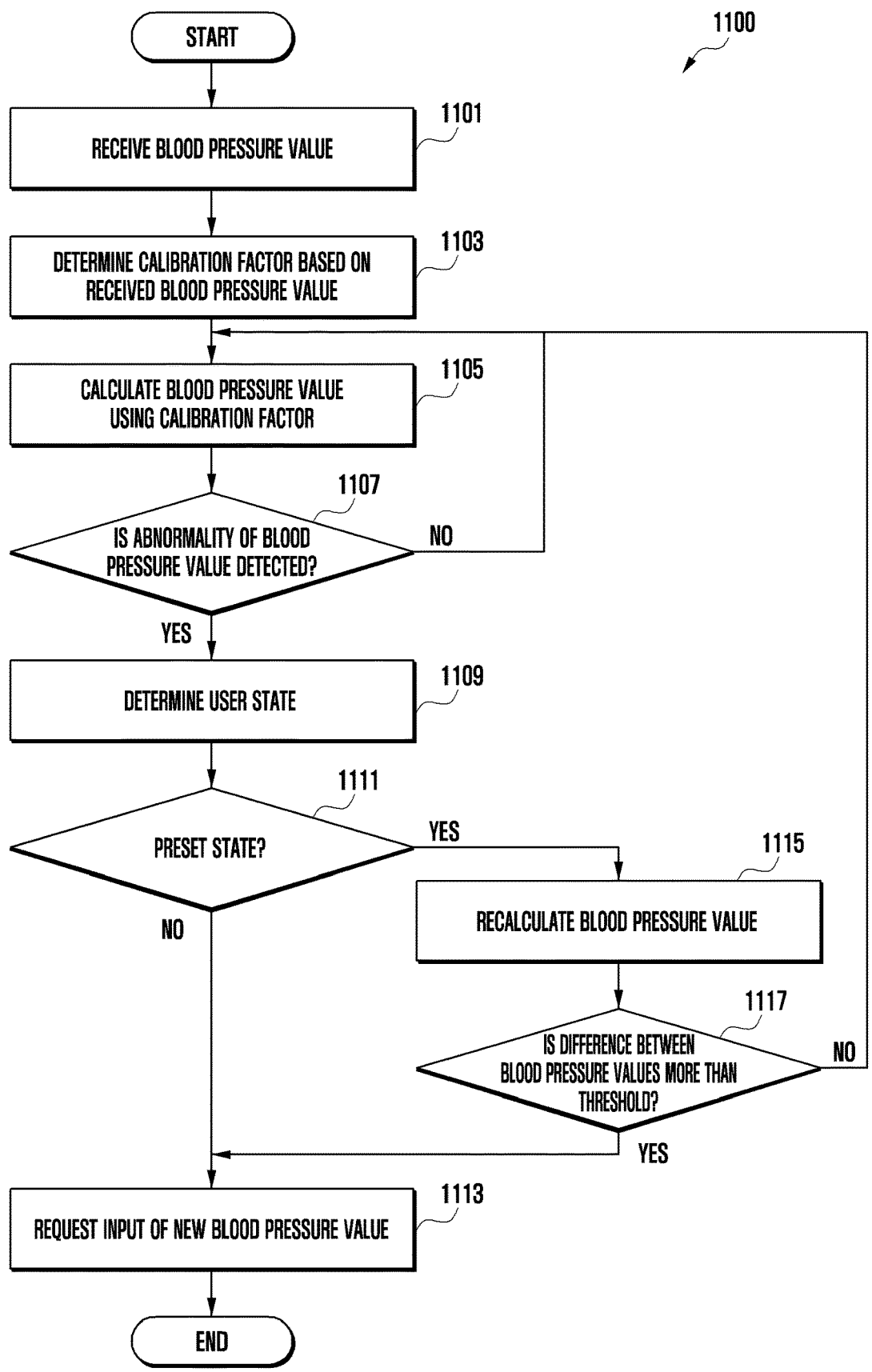
FIG. 11 is a flowchart illustrating an example method of guiding a blood pressure calibration time point of an electronic device according to various embodiments.

FIG. 10 is a flowchart illustrating an example method of guiding a blood pressure calibration time point of an electronic device according to various embodiments, and FIG. 11 is a flowchart illustrating an example method of guiding a blood pressure calibration time point of an electronic device according to various embodiments.

FIG. 10 is a flowchart 1000 illustrating an example method of guiding a calibration time point using different parameters according to various embodiments.

Referring to FIG. 10, in operation 1001, the processor (e.g., the processor 120 of FIG. 1) of the electronic device (e.g., the electronic device 101 of FIG. 1 or the electronic device 200 of FIG. 2) according to various embodiments may calculate a blood pressure value using different parameters. The processor 120 may estimate (or calculate) a blood pressure value using sensor data, and the sensor data (e.g., a measurement parameter) acquired according to the kind of the sensor may vary. The parameter is an input value used to calculate a blood pressure value, and if the parameter becomes different, the blood pressure corresponding to the result value may become different. The processor 120 may calculate at least two blood pressure values by changing a parameter or an equation that will be used to calculate a blood pressure. The processor 120 may calculate a first blood pressure value using fifth to seventh parameters, and may calculate a second blood pressure value using first, third, and tenth parameters. The processor 120 may calibrate the calculated blood pressure value, and may store the calibrated blood pressure value in the memory (e.g., the memory 130 of FIG. 1).

For example, the processor 120 may determine a PAT value, an HR value, and a PTT value using the data acquired by the PPG sensor and peripheral sensors (an acceleration meter, a camera, a microphone, and the like), and may calculate a first blood pressure value by applying the determined values to the first PWV algorithm using the PAT value and the HR value (e.g., by applying the determined values to Equation 1). The processor 120 may calculate a second blood pressure value by applying the determined values to the second PWV algorithm using the PTT value (e.g., by applying the determined values to Equation 2). The processor 120 may determine the PTT value and the values of the blood pressure features using the data acquired by the PPG sensor, may calculate the first blood pressure value using the PWV algorithm using the PTT value, and may calculate the second blood pressure value by applying the PWA algorithm using the blood pressure feature values.

In operation 1003, the processor 120 may determine whether the difference between the blood pressure values is more than the threshold. If the body state of the user changes, the difference between the blood pressure values calculated using different parameters may become larger. The processor 120 may determine a change of the body state of the user based on whether the difference between the blood pressure values is more than the threshold value. Operation 1003 is the same as or similar to operation 807, and a detailed description thereof will not be repeated here. The processor 120 may perform operation 1005 when the difference between the blood pressure values is more than the threshold (e.g., YES), and may return to operation 1001 when the difference between the blood pressure values is less than or equal to the threshold value (e.g., NO).

When the difference between the blood pressure values is more than the threshold (e.g., YES), in operation 1005, the processor 120 may guide a calibration time point. The processor 120 may determine that a calibration time point is necessary when the difference between the blood pressure values is more than the threshold, and may provide guide information related to the calibration time point. Operation 1005 is the same as or similar to operation 811, and a detailed description thereof will not be repeated here.

In operation 1007, the processor 120 may determine whether a new blood pressure value (e.g., blood pressure information) is input. The user may input the blood pressure value calculated using the cuff hemodynamometer to the electronic device 101 while viewing the blood pressure input request message displayed on the display (e.g., the display device 160 of FIG. 1 or the display 220 of FIG. 2) by operation 1005. The processor 120 may determine whether a new blood pressure is input by the user after the blood pressure input request message is provided. The processor 120 may perform operation 1009 when the blood pressure information is input (e.g., YES), and may perform operation 1008 when the blood pressure information is not input (e.g., NO).

When blood pressure information is not input (e.g., NO), in operation 1008, the processor 120 may guide a precision of the blood pressure value. The processor 120 may calculate a blood pressure value consistently using the previously used calibration factor until a new blood pressure value is input even though an error is generated in calculating the blood pressure. The processor 120 may guide a precision of blood pressure when a blood pressure is provided by a request of the user. For example, the processor 120 may guide that the precision of the calculated blood pressure is low.

When blood pressure information is input (e.g., YES), in operation 1009, the processor 120 may perform a blood pressure calibration process. The blood pressure calibration process may include an operation of storing a newly input blood pressure value, determining a calibration factor (e.g., a constant value) using the stored blood pressure value, and calculating (and calibrating) the blood pressure value using the determined calibration factor. The blood pressure calibration process may include an operation of FIG. 4.

FIG. 11 is a flowchart 1100 illustrating an example method of guiding a calibration time point using a calibration factor according to various embodiments.

Referring to FIG. 11, in operation 1101, the processor (e.g., the processor 120 of FIG. 1) of the electronic device (e.g., the electronic device 101 of FIG. 1 or the electronic device 200 of FIG. 2) according to various embodiments may receive a blood pressure value. The blood pressure may be calculated through blood pressure reference equipment that calculates a blood pressure value by applying pressure to the brachial muscle of the user. For example, the blood pressure may include a systolic blood pressure (SBP) and a diastolic blood pressure (DBP). The processor 120 may receive (or be input) the blood pressure value from the user, and may store the input blood pressure value in the memory (e.g., the memory 130 of FIG. 1). Operation 1101 is the same as or similar to operation 401, and a detailed description thereof will be omitted.

In operation 1103, the processor 120 may determine a calibration factor based on the received blood pressure value. The calibration factor may be a constant value used for calculating or calibrating a blood pressure. The processor 120 may determine calibration factors (e.g., $a_1$, $a_2$, $b_1$, $b_2$, and $c_1$) using the blood pressure values. The processor 120 may store the calibration factors in the memory 130, and may be used during the blood pressure calibration. The calibration factor may be determined differently for respectively algorithms. For example, the calibration factor used in the PWA and the calibration factor used in the PWV may be the same or different. Further, a plurality of equations used for the blood pressure calculation method (e.g., the PWA and the PWV) may be different for the equations.

In operation 1105, the processor 120 may measure (calculate) a blood pressure value using the calibration factor. The processor 120 may analyze the waveform of a pulse using sensor data, may extract a feature point having a high correlation with the blood pressure from the analyzed pulse waveform, and may calculate a blood pressure value using the feature point (e.g., the PWA) Further, the processor 120 may calculate a blood pressure value by measuring a blood flow time using a time point at which blood starts and a time point at which the blood arrives, and calculating the velocity of the blood flow (e.g., the PWV). The processor 120 may calculate two or move blood pressure values using different parameters, equations, or blood pressure calculation methods. The processor 120 may calibrate the blood pressure value calculated using the calibration factor.

In operation 1107, the processor 120 may determine whether an abnormality of blood pressure is detected. For example, the processor 120 may determine whether the difference between the blood pressure values is more than the threshold. Because the processor 120 calculates two or more blood pressure values using different blood pressure calculation methods or different parameters, there may be a difference between the blood pressure values. The processor 120 may determine that the blood pressure value is normally calculated and calibrated when the difference between the blood pressure values is less than the threshold, and may determine that there is an error (or a problem) in calculation of the blood pressure when the difference between the blood pressure values is the threshold or more. The processor 120 may perform operation 1109 when an abnormality of blood pressure is detected (YES), and may return to operation 1105 when an abnormality of blood pressure is not detected (NO).

When an abnormality of blood pressure is detected (YES), in operation 1109, the processor 120 may determine the user state. The user state also may include at least one of a static state, a dynamic state, a sleep state, or an exercise state. The processor 120 may determine the user state if an abnormality of blood pressure is detected to determine whether the user state is a cause of the error in the calculation of the blood pressure. The processor 120 may determine the user state to determine whether the user state (or posture) is not problematic in calculation of the blood pressure. Operation 1109 is the same as or similar to operation 801, and a detailed description thereof will not be repeated here.

In operation 1111, the processor 120 may determine whether the user state is a preset state. The preset state may include a static state or a sleep state. The processor 120 may perform operation 1113 when the user state is not a preset state (e.g., NO), and may perform operation 1115 when the user state is the preset state (e.g., YES).

When the user state is not the present state (e.g., NO), in operation 1113, the processor 120 may request an input of a new blood pressure value (e.g., a third blood pressure value). The processor 120 may provide a guide for inputting a blood pressure value measured by a cuff hemodynamometer to the user.

When the user state is a present state (e.g., YES), in operation 1115, the processor 120 may recalculate the blood pressure value. The processor 120 may recalculate the blood pressure value when the user state is a state in which there is no problem in calculation of the blood pressure value. The processor 120 may recalculate the blood pressure value with those that are different from the parameter, the equation, or the blood pressure calculation method used in operation 1105. The processor 120 may recalculate two or move blood pressure values using different parameters, equations, or blood pressure calculation methods.

In operation 1117, the processor 120 may determine whether the difference between the recalculated blood pressure values is more than the threshold. The processor 120 may perform operation 1113 when the difference between the blood pressure values is more than the threshold (e.g., YES), and may return to operation 1105 when the difference between the blood pressure values is less than or equal to the threshold value (e.g., NO).

Figure 12:
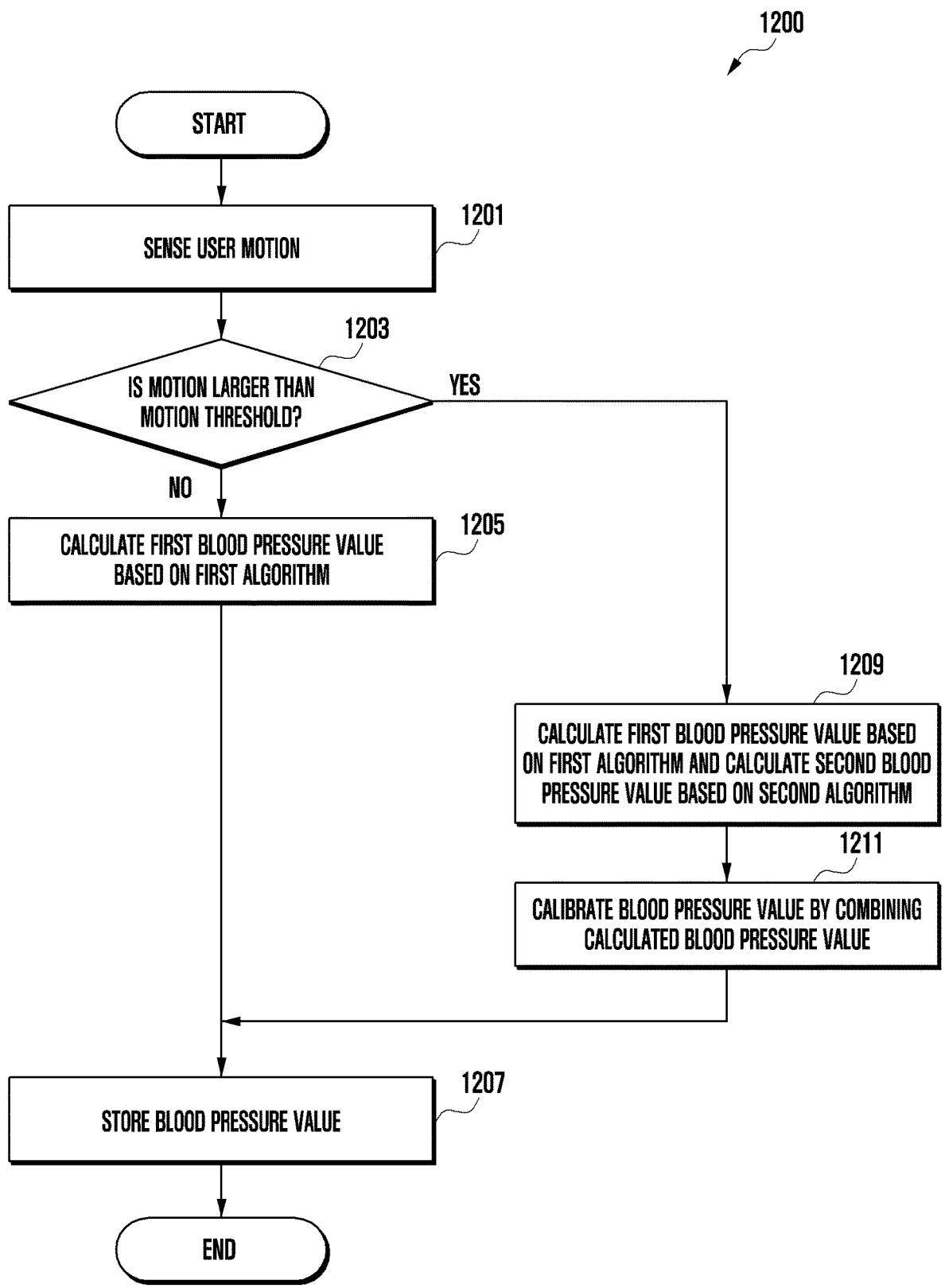
FIG. 12 is a flowchart illustrating an example method of calculating a blood pressure in an electronic device according to various embodiments.
Figure 13:
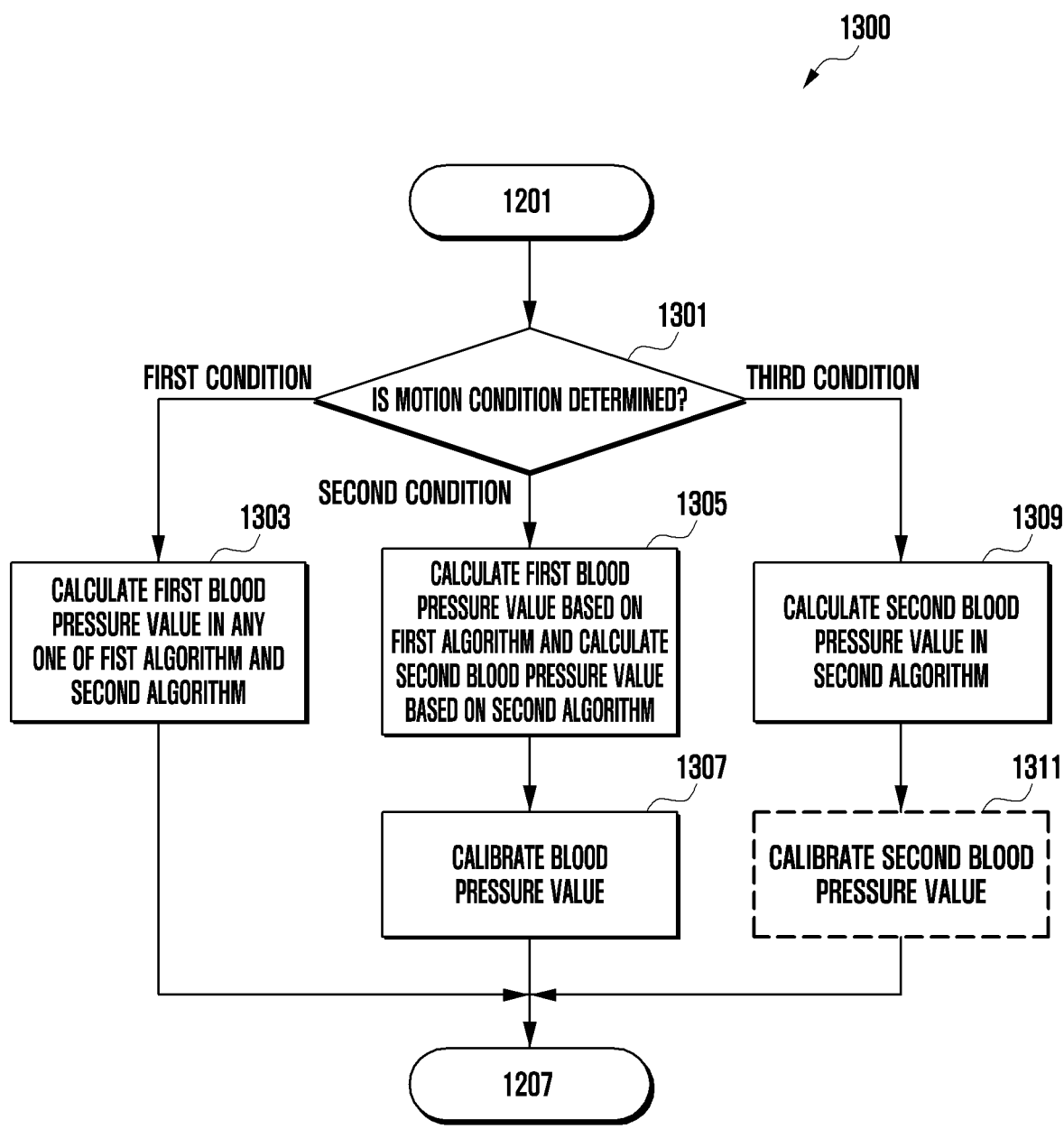
FIG. 13 is a flowchart illustrating an example method of calculating a blood pressure in an electronic device according to various embodiments.

FIG. 12 is a flowchart illustrating an example method of calculating a blood pressure in an electronic device according to various embodiments, and FIG. 13 is a flowchart illustrating an example method of calculating a blood pressure in an electronic device according to various embodiments.

FIG. 12 is a flowchart 1200 illustrating an example method of calculating a blood pressure value based on a user motion according to various embodiments.

Referring to FIG. 12, in operation 1201, the processor (e.g., the processor 120 of FIG. 1) of the electronic device (e.g., the electronic device 101 of FIG. 1 or the electronic device 200 of FIG. 2) according to various embodiments may sense (or detect) a user motion. The processor 120 may sense a motion of the user using acceleration data. The user motion may be similar to the user state. For example, the user motion may be a state having a motion or a state having no motion. Further, the user motion may be classified into high, middle, and low, and first to four steps according to the degree of the motion. The classification of the user motion is simply for helping understanding of the disclosure, and is not intended to limit the disclosure.

In operation 1203, the processor 120 may determine whether user motion is more than a motion threshold. For example, the motion threshold may be a reference for determining a blood pressure calculation method according to a motion. For example, when the user motion is classified into a state having a motion or a state having no motion, the motion threshold may be a state having a motion. When the user motion is classified into steps 1 to 4, the motion threshold may be step 2 or step 3. The processor 120 may perform operation 1209 when the motion is more than the motion threshold (e.g., YES), and may perform operation 1205 when the motion is less than or equal to the motion threshold value (e.g., NO).

When the motion is less than or equal to the motion threshold (e.g., NO), in operation 1205, the processor 120 may calculate a first blood pressure value based on the first algorithm. For example, the processor 120 may calculate the first blood pressure value by any one of the PWA or PAV when there is no motion. When there is no motion in the electronic device 101, a method that will be used to calculate a blood pressure may be set in advance. Further, the processor 120 may select at least one of the PWA or the PWV whenever the blood pressure is calculated according to the parameter.

In operation 1207, the processor 120 may store the calculated blood pressure value. The processor 120 may calibrate the calculated blood pressure value, and may store the calibrated blood pressure value in the memory (e.g., the memory 130).

When the motion is more than the motion threshold (e.g., YES), in operation 1209, the processor 120 may calculate a first blood pressure value based on a first algorithm, and may calculate a second blood pressure value based on a second algorithm. For example, the processor 120 may calculate a first blood pressure value using the PWA, and may calculate a second blood pressure value using the PWV. The processor 120 may determine the PTT value and the values of the blood pressure features using the data acquired by the PPG sensor and peripheral sensors (an acceleration meter, a camera, a microphone, and the like), may calculate the first blood pressure value using the PWV algorithm using the PTT value, and may calculate the second blood pressure value by applying the PWA algorithm using the blood pressure feature values.

In operation 1211, the processor 120 may combine the calculated blood pressure values to calibrate the blood pressure value. For example, the processor 120 may calibrate the first blood pressure value and the second blood pressure value to one blood pressure value. The processor 120 may perform operation 1207 and store the calibrated blood pressure value in the memory 130.

FIG. 13 is a flowchart 1300 illustrates an example blood pressure calculation operation according to a user motion of FIG. 12 according to various embodiments.

Referring to FIG. 13, in operation 1301, the processor (e.g., the processor 120 of FIG. 1) of the electronic device (e.g., the electronic device 101 of FIG. 1 or the electronic device 200 of FIG. 2) according to various embodiments may determine a motion condition. For example, the processor 120 may determine to which condition the user motion sensed in operation 1201 of FIG. 12 corresponds. The user motion may be classified into condition 1 in which the user state is a sleep state, condition 2 in which the user state is a static state, condition 3 in which the user state is a dynamic state, and step 4 in which the user state is an exercise state. The processor 120 cannot calculate a blood pressure because it corresponds to an exercise state when the user motion corresponds to step 4, and may not calculate a blood pressure. The processor 120 may perform operation 1303 while determining the condition as a first condition when the user motion is step 1, may perform operation 1305 while determining the condition as a second condition when the user motion is step 2, and may perform operation 1309 while determining the condition as a third condition when the user motion is step 3.

In the first condition, in operation 1303, the processor 120 may calculate a first blood pressure value in any one of the first algorithm or the second algorithm. The processor 120 may calculate the blood pressure value by any one of the PWA or PAV when there is no user motion (e.g., step 1). Because a precise blood pressure value can be obtained when there is no motion, the processor 120 may calculate a blood pressure value in any one of the two methods. Further, a method for calculating a blood pressure value when there is no motion may be set in the electronic device 101. Further, the processor 120 may select any one method according to the sensed data. The processor 120 may perform operation 1207 of FIG. 12 if operation 1303 is completed.

In the second condition, in operation 1305, the processor 120 may calculate the first blood pressure value in the first algorithm, and may calculate the second blood pressure value in the second algorithm. The processor 120 may calculate the blood pressure value in the PWA algorithm and the PWV algorithm when the user motion is step 2. The processor 120 may calculate the blood pressure value through both the two methods to reduce an error in calculation of the blood pressure. For example, the processor 120 may determine the PTT value and the values of the CO and the TPR using the data acquired by the PPG sensor, may calculate the first blood pressure value using the PWV algorithm using the PTT value, and may calculate the second blood pressure value by applying the PWA algorithm using the values of the CO and the TPR.

In operation 1307, the processor 120 may calibrate the blood pressure value. For example, the processor 120 may combine the first blood pressure value and the second blood pressure value to calibrate them to one blood pressure value. The processor 120 may determine a calibration factor used in a blood pressure calibration in the second condition, and may calibrate the blood pressure value using the determined calibration factor. The processor 120 may perform operation 1207 of FIG. 12 if operation 1307 is completed.

In the third condition, in operation 1309, the processor 120 may calculate the second blood pressure value in the second algorithm. The processor 120 may calculate the blood pressure value in, among the PWA and the PWV, the PWV that is robust to a motion when the user motion is step 3. The processor 120 may determine a PAT value, an HR value, and a PTT value using the data acquired by the PPG sensor, and may calculate a blood pressure value by applying the determined values to the first PWV algorithm using the PAT value and the HR value (e.g., by applying the determined values to Equation 1). The processor 120 may calculate a blood pressure value by applying the determined values to the second PWV algorithm using the PTT value (e.g., by applying the determined values to Equation 2).

In operation 1311, the processor 120 may calibrate the blood pressure value. For example, the processor 120 may calibrate a blood pressure value to reduce an error in calculation of a blood pressure. Operation 1311 may be omitted according to the degree of motion. The processor 120 may perform operation 1207 of FIG. 12 if operation 1311 is completed.

According to various example embodiments, a personalized blood pressure calibration time point can be detected and informed of by monitoring a difference between blood pressures calculated by two different blood pressure calculation methods.

According to various example embodiments, a blood pressure can be calculated more precisely utilizing an electronic device, by detecting an abnormality of a blood pressure calculated by the electronic device based on a blood pressure calculated by a blood pressure reference device (e.g., a cuff hemodynamometer) and requesting a new blood pressure value calculated by the cuff hemodynamometer.

The embodiments of the disclosure disclosed herein and illustrated in the drawings are merely examples presented for illustrative purposes and to aid in the understanding of the disclosure, and are not intended to limit the scope of the disclosure. Therefore, it should be understood that, in addition to the embodiments disclosed herein, all modifications and changes or modified and changed forms derived from the technical idea of the disclosure fall within the scope of the disclosure.

What is claimed is:

1. An electronic device comprising:
 a housing;
 a user interface disposed in a first part of the housing;
 a photoplethysmogram (PPG) sensor disposed to be exposed through a second part of the housing, the PPG sensor configured to calculate a blood pressure value while contacting a portion of a body;
 at least one sensor;
 a wireless communication circuit disposed in an interior of the housing;
 a processor disposed in the interior of the housing, and operatively connected to the user interface, the PPG sensor, the at least one sensor, and the wireless communication circuit; and
 a memory operatively connected to the processor,
 wherein the memory stores instructions that, when executed by the processor, are configured to control the electronic device to:
 receive first data from the at least one sensor;
 receive second data from the PPG sensor based at least in part on the received first data;
 determine a pulse arrival time (PAT) value, a heart rate (HR) value, and a pulse transit time (PTT) value from the second data;
 calculate a first blood pressure value (BP1) and a second blood pressure value (BP2) by applying the determined values to pulse wave velocity (PWV) algorithms including:

$$BP1 \cong a_1 PAT + b_1 HR + c_1, \text{ and}$$

$$BP2 \cong a_2 \ln(PTT) + b_2,$$

wherein $a_1$, $a_2$, $b_1$, $b_2$, and $c_1$ are constant values for matching blood pressure values measured during calibration with blood pressure values measured by a cuff hemodynamometer;
 determine whether the difference between the first blood pressure value and the second blood pressure value is more than a threshold;
 determine a user state if the difference between the first blood pressure value and the second blood pressure value is more than the threshold;
 recalculate two or more blood pressure values using different at least one of parameters, equations, or blood pressure calculation methods, if the user state is a present state; and
 provide guide information related to a calibration time point through the user interface, and request an input of a new blood pressure value, if the user state is not the present state.

2. The electronic device of claim 1, wherein the instructions, when executed by the processor, control the electronic device to:
 receive second data from the PPG sensor based on the first data being a selected threshold value or less.

3. The electronic device of claim 1, wherein the at least one sensor includes at least one of an acceleration sensor, a proximity sensor, a temperature sensor, or an iris sensor.

4. The electronic device of claim 1, wherein the instructions, when executed by the processor, control the electronic device to:

store the calculated blood pressure value in the memory based at least in part on the difference between the first blood pressure value and the second blood pressure value.

5. The electronic device of claim 1, wherein the electronic device comprises a wearable device.

6. The electronic device of claim 1, wherein the instructions, when executed by the processor, control the electronic device to:
receive a third blood pressure value input in response to the guide information; and
store the third blood pressure value in the memory.

7. The electronic device of claim 6, wherein the instructions, when executed by the processor, control the electronic device to:
guide a precision of blood pressure until the third blood pressure value is input.

8. The electronic device of claim 6, wherein the instructions, when executed by the processor, control the electronic device to:
determine the constant values based at least in part on the third blood pressure value; and
calculate the first blood pressure value and the second blood pressure value based at least in part on the determined constant value.

9. An electronic device comprising:
a housing;
a user interface disposed in a first part of the housing;
a photoplethysmogram (PPG) sensor disposed to be exposed through a second part of the housing, the PPG sensor configured to calculate a blood pressure value while facing a portion of a body;
a wireless communication circuit disposed in the interior of the housing;
a processor disposed in the interior of the housing, and operatively connected to the user interface, the PPG sensor, and the wireless communication circuit; and
a memory operatively connected to the processor,
wherein the memory stores instructions that, when executed by the processor, are configured to control the electronic device to:
receive data from the PPG sensor;
determine a PAT value, an HR value, and a PTT value by determine one or more parameters from the received data;
calculate a first blood pressure value and a second blood pressure value based at least in part on at least two parameters of the determined at least one parameter which do not overlap, and a correction factor to a first pulse wave velocity (PWV) algorithm using the PAT value and the HR value and a second PWV algorithm using the PTT value;
determine whether the difference between the first blood pressure value and the second blood pressure value is more than a threshold;
determine a user state if the difference between the first blood pressure value and the second blood pressure value is more than a threshold;
recalculate two or move blood pressure values using different at least one of parameters, equations, or blood pressure calculation methods, if the user state is a present state; and
provide information related to a calibration through the user interface and request an input of a new blood pressure value, if the user state is not the present state.

10. The electronic device of claim 9, wherein the instructions, when executed by the processor, control the electronic device to:
guide a precision of blood pressure until a third blood pressure value is input via the user interface.

11. An electronic device comprising:
a housing;
a user interface disposed in a first part of the housing;
a photoplethysmogram (PPG) sensor disposed to be exposed through a second part of the housing, the PPG sensor configured to calculate a blood pressure value while contacting a portion of a body;
a wireless communication circuit disposed in the interior of the housing;
a processor disposed in the interior of the housing, and operatively connected to the user interface, the PPG sensor, and the wireless communication circuit; and
a memory operatively connected to the processor,
wherein the memory stores instructions that, when executed by the processor, are configured to control the electronic device to:
receive data from the PPG sensor;
determine a pulse transit time (PTT) value, a cardiac output (CO) value, and a total peripheral resistance (TPR) value from the received data;
calculate a first blood pressure value and a second blood pressure by applying the determined values to a first pulse wave velocity (PWV) algorithm using the PTT value and a second pulse wave analysis (PWA) algorithm using the CO value and the TPR value;
determine whether the difference between the first blood pressure value and the second blood pressure value is more than a threshold;
determine a user state if the difference between the first blood pressure value and the second blood pressure value is more than a threshold;
recalculate two or more blood pressure values using different at least one of parameters, equations, or blood pressure calculation methods, if the user state is a present state; and
provide information related to the calibration through the user interface and request an input of a new blood pressure value, if the user state is not the present state.

12. The electronic device of claim 11, wherein the user state comprises at least one of a static state, a dynamic state, a sleep state, or an exercise state, and
wherein the preset state is the static state or the sleep state.

13. The electronic device of claim 11, wherein the instructions, when executed by the processor, control the electronic device to:
delete a blood pressure value stored in the memory in response to input of a third pressure blood pressure value, and store the third blood pressure value; and
recalculate the first blood pressure value and the second blood pressure value based at least in part on the stored third blood pressure value.

14. The electronic device of claim 11, wherein the instructions, when executed by the processor, control the electronic device to:
calculate the first blood pressure value or the second blood pressure value with any one of the first PWV algorithm or the second PWA algorithm based on a motion corresponding to a first condition.

15. The electronic device of claim 11, wherein the instructions, when executed by the processor, control the electronic device to:

calculate the first blood pressure value with the first PWV algorithm and calculate the second blood pressure value with the second PWA algorithm based on a motion corresponding to a second condition.

16. The electronic device of claim 11, wherein the instructions, when executed by the processor, control the electronic device to:

determine whether a calibration is necessary using the first blood pressure value calculated by the first PWV algorithm and the second blood pressure value calculated by the second PWA algorithm based on a motion corresponding to a third condition.

* * * * *